United States Patent
Yowe

(10) Patent No.: US 6,326,481 B1
(45) Date of Patent: Dec. 4, 2001

(54) MOLECULES OF THE AIP-RELATED PROTEIN FAMILY AND USES THEREOF

(75) Inventor: David Yowe, North Quincy, MA (US)

(73) Assignee: Millennium Pharmaceuticals. Inc., Cambridge, MA (US)

( * ) Notice: Subject to any disclaimer, the term of this patent is extended or adjusted under 35 U.S.C. 154(b) by 0 days.

(21) Appl. No.: 09/324,455

(22) Filed: Jun. 2, 1999

Related U.S. Application Data

(60) Provisional application No. 60/087,761, filed on Jun. 2, 1998.

(51) Int. Cl.[7] .............................. C07K 1/00; C07K 14/00; C07K 17/00; C07H 21/04; C07H 1/00

(52) U.S. Cl. ............................ 536/23.5; 536/1; 536/1.11; 536/18.7; 536/22.1; 536/23.1; 536/23.5; 530/350

(58) Field of Search .............................. 536/1, 1.11, 18.7, 536/22.1, 23.1, 23.5; 530/350

(56) References Cited

FOREIGN PATENT DOCUMENTS

WO 97/06255    2/1997   (WO) .
WO 97/40847   11/1997   (WO) .

OTHER PUBLICATIONS

Ambrosini et al., "Novel anti–apoptosis gene, surviving, expressed in cancer and lymphoma" Nature Med. 3:917–921, 1997.
Chinnaiyan et al., "FADD, a novel death domain–containing protein, interacts with the death . . . " Cell 81:505–512, 1995.
Clem et al., "The iap genes: unique arbitrators of cell death" Trends in Cell. Biol. 7:337–339, 1997.
Cotman et al., "A potential role for apoptosis in neurodegeneration and alzheimer's disease" Molecular Neurobiology 10:19–45, 1995.
Chu et al., "Suppression of tumor necrosis factor–induced cell death by inhibitor of apoptosis . . . " Proc. Nat'l. Acad. Sci. USA 94:10057–10062, 1997.
Duckett et al., "A conserved family of cellular genes related to the baculovirus iap gene . . . " The EMBO Journal 15(11):2685–2694, 1996.
Hay et al., "Drosphila homologs of baculovirus inhibitor of apoptosis proteins function . . . " Cell 83:1253–1262, 1995.
Johnson et al., "Neuronal apoptosis: Current understanding of molecular mechanisms and . . . " J. of Neurotrauma 12(5):843–852, 1995.
Liston et al., "Suppression of apoptosis in mammalian cells by NAIP and a related family of IAP genes" Nature 379:349–353, 1996.
McDonnell et al., "Implications of apoptotic cell death regulation in cancer therapy" Seminars in Cancer Biology 6:53–60, 1995.
Reed, J., "Double identity for proteins of the Bcl–2 family" Nature 387:773–776, 1997.
Roy et al., "The c–IAP–1 and c–IAP–2 proteins are direct inhibitors of specific caspases" The EMBO Journal 16(23):6914–6925, 1997.
Saurin et al., "Does this have a familiar ring?" Trends in Biochem. Sci. 21:208–214, 1996.
Spencer et al., "Controlling signal transduction with synthetic ligands" Science 262:1019–1024, 1993.
Thompson, C., "Apoptosis in the pathogenesis and treatment of disease" Science 267:1456–1462, 1995.
GenBank Accession No. L49441, Hay et al., Jan. 18, 1996.
GenBank Accession No. U45881, Liston et al., Feb. 16, 1996.
GenBank Accession No. U38809, Uren et al., Sep. 17, 1996.
GenBank Accession No. U32373, Duckett et al., Jul. 12, 1996.
GenBank Accession No. Q13489, Rothe et al., Jul. 15, 1999.
GenBank Accession No. Q13490, Rothe et al.,May 30, 2000.
GenBank Accession No. U45880, Liston et al., Feb. 16, 1996.
GenBank Accession No. U36842, Uren et al., Jun. 5, 1996.
GenBank Accesssion No. U40945, Wilson et al., Nov. 25, 1995.
GenBank Accession No. U12593, Zhou et al., Feb. 3, 1995.
GenBank Accession No. U66469, Madden, S.L., Dec. 11, 1996.
GenBank Accession No. Z77655, Sims, M.A., Dec. 10, 1999.
GenBank Accession No. Z81505, Baynes, C., Dec. 10, 1999.
GenBank Accession No. AF003534, Bahr et al., Jan. 2, 1998.
Horrevoets et al., "Vascular endothelial genes that are reponsive to tumor necrosis . . ." Medline Abstract, Blood 15(93):3418–3431, 1999.
You M. et al., "ch–IAP1, a member of the inhibitor–of–apoptosis protein family1, is a mediator . . .".
Medline Abstract, Mol. Cell. Biol. 17(12):7328–7341, 1997.
Nucleic acid database, Accession #AA452343, 1997.*
Amino acid and nucleic acid database, Accession #AA452343, 1997.*
Amino acid and nucleic acid database, Accession #R59956, 1995.*

(List continued on next page.)

Primary Examiner—Anthony C. Caputa
Assistant Examiner—Alana M. Harris
(74) Attorney, Agent, or Firm—Fish & Richardson, P.C.

(57) ABSTRACT

Novel AIP-6 polypeptides, proteins, and nucleic acid molecules are disclosed. In addition to isolated, full-length AIP-6 proteins, the invention further provides isolated AIP-6 fusion proteins, antigenic peptides and anti-AIP-6 antibodies. The invention also provides AIP-6 nucleic acid molecules, recombinant expression vectors containing a nucleic acid molecule of the invention, host cells into which the expression vectors have been introduced and non-human transgenic animals in which a AIP-6 gene has been introduced or disrupted. Diagnostic, screening and therapeutic methods utilizing compositions of the invention are also provided.

20 Claims, 4 Drawing Sheets

OTHER PUBLICATIONS

Hillier et al. Generation and Analysis of 280,000 Human Expressed Sequence Tags. Genome Resarch 6:807–828, 1996.*

Amino acid and nucleic acid database, Accession #AA135205, 1997.*

Amino acid and nucleic acid database, Accession #G25120, 1996.*

Nucleic acid database, Accession #AA579643, 1997.*

* cited by examiner

→ (SEQ ID NO:1)
GAATTCCCGGGTCGACCCACGCGTCCGGGAGGTCGGCAGTGTGAGGAGCTGCTATGGTGC
                                        (SEQ ID NO:3)→
TGAGTTTCCTGGTAGAGCCGGCCGAGCTGAGGCGGTCGCGGCCATGAAGGCGGGTGCCAC

GTCTATGTGGGCTTCGTGCTGTGGGCTGCTGAATGAAGTCATGGGAACTGGAGCTGTCAG

GGGCCAGCAGTCAGCATTTGCAGGAGCCACCGGTCCATTCAGATTTACACCAAACCCTGA

GTTTTCCACCTACCCACCAGCAGCTACGGAAGGGCCCAACATAGTTTGTAAAGCCTGTGG

GCTTTCATTTTCAGTCTTTAGAAAGAAGCATGTTTGCTGTGACTGCAAGAAGGATTTTTG

CTCCGTTTGTTCAGTCTTACAAGAAAATCTCCGTAGATGTTCTACTTGTCACTTATTACA

AGAGACAGCATTTCAGCGCCCTCAGTTAATGCGACTGAAGGTGAAGGACCTGCGGCAGTA

TCTCATTCTGAGAAATATACCCATAGATACTTGTCGTGAGAAGAAGACTTGGTGGATCT

AGTACTGTGCCATCATGGACTAGGCTCTGAGGACGACATGGACACAAGCAGTCTGAATTC

TTCAAGGTCCCAGACTTCTAGCTTTTTTACACGTTCGTTTTTTTCAAACTATACAGCCCC

CTCTGCTACTATGTCTTCGTTTCAGGGAGAGCTTATGGATGGAGACCAAACATCCAGATC

TGGAGTGCCGGCACAGGTACAAAGTGAAATCACTTCAGCAAACACAGAAGATGATGATGA

CGACGATGATGAGGATGATGATGATGAAGAAGAAAACGCAGAGGATCGGAACCCCGGGCT

CTCCAAGGAGAGAGTGAGAGCTTCACTGTCTGACTTGTCAAGCCTTGATGATGTGGAAGG

AATGAGCGTGCGCCAGCTGAAGGAAATTCTGGCTCGGAATTTTGTCAACTATTCTGGCTG

TTGTGAAAAATGGGAACTGGTAGAGAAAGTAAACCGGTTATACAAAGAGAATGAAGAAAA

CCAAAAGTCCTATGGCGAGCGGCTGCAGCTGCAGGATGAGGAAGACGACAGCCTGTGTCG

CATCTGCATGGATGCCGTCATCGACTGTGTCCTACTGGAGTGTGGGCACATGGTTACCTG

CACCAAGTGCGGCAAGCGCATGAGTGAGTGTCCATCTGCCGGCAGTATGTGGTGCGAGC

CGTGCACGTGTTCAAGTCCTGAAACAGGCTCCCCTCACCAGGACAGTCACCCCCAAACTT

GACCCCAAACATTTCAATGCACAGAAGGGACTGGAAAGTTATGTTCAAAGGCTGAAGCTA

TTTTAAAACATTATTTTGACTACTAAGTGGGACAGAAAGATCCATCCTGAGTTGTGGAA

ACATTGGTCCATGCCGTGAGCCTGTCTGCCTGTGGACACGTGAGCTTCCCGGGCTCAGCT

GGGCTTTATCACACATCCCGTGAACACTCATTGAAGTCAGCCTGTTTGCGCCATGTGGGC

FIG. 1A

ATCAGCCACTGCTGTCTTGGGAGGACACTTATCCTGTTCTCTTATTTCCCCTTCATCCTA
TTTTTAACTTAAACTGCTCAGATGTTTGAAACTTCTGTCCTCTTTGGATGAGATCAGTGT
CCACAAGTGGCCGACATGGAACATGCTGAGCAGTGGCTCCTCTGAATGTTCACTTTATTA
GTCATGTATATTTTAAATGCTAACATTTGATGAATGTAAGTTTCCACATTGTTGCTGTTT
CTGCATTTAAACATAATTGGGAACAACTGACATTCTCTAGTCGACTGCCAGGGCCTTAGA
CTCCACATGTCCATTTTTGTTCAGGTATAGCTTTTTATAGCAAGGGCTGCATCTAGCTTC
TTTTATTAGAAGTGTGTGTGCTAAATTCCTTATTAATGTGTAATCAGTTTACACTGTTTT
GTATAGTGAAGGTGTATTTTCAGTGCTACCCGCTAGCTGATTTTAACTTTAGGAATAAAA
TTAGTTTTAAAAAAAAAAAAAAAAAAAGGGCGGCCGCTGCGGCCGC

FIG. 1B

→ (SEQ ID NO:2)
MKAGATSMWASCCGLLNEVMGTGAVRGQQSAFAGATGPFRFTPNPEFSTYPPAATEGPNI

VCKACGLSFSVFRKKHVCCDCKKDFCSVCSVLQENLRRCSTCHLLQETAFQRPQLMRLKV

KDLRQYLILRNIPIDTCREKEDLVDLVLCHHGLGSEDDMDTSSLNSSRSQTSSFFTRSFF

SNYTAPSATMSSFQGELMDGDQTSRSGVPAQVQSEITSANTEDDDDDDEDDDDEEENAE

DRNPGLSKERVRASLSDLSSLDDVEGMSVRQLKEILARNFVNYSGCCEKWELVEKVNRLY
            (SEQ ID NO:4)→
KENEENQKSYGERLQLQDEEDDSLCRICMDAVIDCVLLECGHMVTCTKCGKRMSECPICR

QYVVRAVHVFKS

FIG. 2

MOLECULES OF THE AIP-RELATED PROTEIN FAMILY AND USES THEREOF

RELATED APPLICATION INFORMATION

This application claims priority from provisional application serial No. 60/087,761, filed Jun. 2, 1998.

The invention relates to the field of apoptosis.

BACKGROUND OF THE INVENTION

The human body contains various tissues that continually undergo a process of self-renewal, whereby older cells in the tissue die and are replaced by new cells. In order to maintain a constant number of cells within a particular tissue, it is important that the number of newly produced cells equals the number of cells that die. This homeostasis is maintained by committing differentiated cells to a deliberate and genetically controlled cellular process known as programmed cell death or apoptosis. Apoptotic cells undergo characteristic morphological changes including cell shrinkage, loss of mitochondrial function, and both nuclear condensation and fragmentation. These cellular alterations provide structures suitable for recognition and clearence by proximal phagocytosing cells. Importantly, apoptosis occurs without inducing an inflammatory response and without damage to surrounding cells.

Apoptosis can be induced by a number of unrelated stimuli. However, recent evidence suggests that regardless of the initiating stimulus, apoptosis is signalled through a common pathway. Numerous genes associated with this pathway have been identified, but the way in which their products interact to execute the apoptotic program is still poorly understood.

Defects in the apoptotic pathway can contribute to the onset or progression of various pathological conditions. In humans, the failure of cells to undergo appropriate apoptosis can lead to cancer, autoimmune diseases and viral infection. Conversely, accelerated rates of apoptosis can lead to e.g., neurodegenerative disorders and osteoporosis. Thus, controlling inappropriate cell death or cell survival is important for the treatment of a variety of human diseases.

Amongst the few proteins known to inhibit cell death are certain members of the Bcl-2 family of proteins (Reed, *Nature* 387:773–776). Recently, another family of anti-apoptotic proteins, IAP (inhibitor of apoptosis), was identified (Clem and Duckett, *Trends in Cell Biology* 7:337–339).

The first IAP gene was identified in baculovirus and since then cellular homologues of IAP have been identified in Drosophila, chickens and humans (Hay et al., *Cell*, 83, 1253–1262, 1995; Duckett et al., *EMBO J.*, 15:2685–2689, 1996; Liston et al., *Nature* 379:349–353, 1996). The IAP proteins are highly conserved through evolution and characteristically contain two types of sequence motifs/domains (Reed, supra). The C-terminus of an IAP typically contains a RING finger motif. This motif is a type of zinc finger motif, and is thought to be involved in protein-protein interactions. However the exact function of the RING finger motif remains elusive (Saurin et al., Trends Biochem Sci 21:208–214, 1996).

The other common sequence motif common to many of the IAPs is a BIR (baculovirus IAP repeat). BIRs, which are situated at the N-terminus of the IAP, normally comprise 2–3 imperfect repeats of approximately 65 amino acid residues each and contain a number of absolutely conserved residues, including $CysX_2Cys$ and $CysX_6His$ motifs (where X is any amino acid). Recent evidence suggests that the BIRS mediate anti-death activity through their involvement in protein-protein interactions (Ambrosini et al., Nature Med 3:917–921, 1997). To date, all IAPs have been found to contain at least one BIR motif. Furthermore, all but two members of the IAP protein family, NAIP (neuronal apoptosis inhibitory protein) and survivin (human IAP homologue), have been found to contain a RING finger motif.

The mechanism of action of an IAP protein is complex. While viral IAP homologues block apoptotic cell death, this is not always the case for the cellular homologues. However, several cellular homologues do possess the ability to block apoptosis. For example, two human IAPs, c-IAP1 and c-IAP2, have been identified as components of the TNF (tumor necrosis factor) receptor signalling complex. These c-IAPs interact with the TRAF-N domain of TRAF1 (TNF receptor associated factor 2) and TRAF2 via the BIRs (Rothe et al., *Cell*, 83:1243–1252, 1995). While the exact function of this interaction is still unknown, recent reports show that c-IAP2 is involved in protecting cells from TNF-induced cell death by activating NF-κB (Chu et al., *PNAS*, 94:10057–10062, 1997). Additionally, c-IAP1 and c-IAP2 inhibit cell death by interfering with specific members of the caspase family of cell death proteases, thereby promoting cell survival (Roy et al., *EMBO J*, 16:6914–6925, 1997).

SUMMARY OF THE INVENTION

The present invention is based, at least in part, on the discovery of a gene encoding an apoptotic inhibitor protein 6 (AIP-6), an intracellular protein that is predicted to be a member of the IAP superfamily. The AIP-6 cDNA described below (SEQ ID NO:1) has a 1116 nucleotide open reading frame (nucleotides 104–1219 of SEQ ID NO:1; SEQ ID NO:3) which encodes a 372 amino acid protein (SEQ ID NO:2). AIP-6 protein possesses a RING finger domain (amino acids 324–358; SEQ ID NO:4). The AIP-6 protein is unique among other IAP proteins in that it does not contain a BIR motif.

The AIP-6 molecules of the present invention are predicted to play a role in apoptosis. Accordingly, in one aspect, this invention provides isolated nucleic acid molecules encoding AIP-6 proteins or biologically active portions thereof, as well as nucleic acid fragments suitable as primers or hybridization probes for the detection of AIP-6-encoding nucleic acids.

The invention features a nucleic acid molecule which is at least 55%, (65%, 75%, 85%, 95%, or 98%) identical to the nucleotide sequence shown in SEQ ID NO:1, or SEQ ID NO:3, or the nucleotide sequence of the cDNA insert of the plasmid deposited with ATCC as Accession Number (the "cDNA of ATCC 209860"), or a complement thereof.

The invention features a nucleic acid molecule which includes a fragment of at least 300, 325, 350, 375, 400, 425, 450, 500, 550, 600, 650, 700, 800, 900, 1000, 1300, 1600, 1900 and 2026) nucleotides of the nucleotide sequence shown in SEQ ID NO:1, or SEQ ID NO:3, or the nucleotide sequence of the cDNA ATCC 209860, or a complement thereof.

The invention also features a nucleic acid molecule which includes a nucleotide sequence encoding a protein having an amino acid sequence that is at least 45% (or 55%, 65%, 75%, 85%, 95%, or 98%) identical to the amino acid sequence of SEQ ID NO:2, or the amino acid sequence encoded by the cDNA of ATCC 209860.

In a preferred embodiment, a AIP-6 nucleic acid molecule has the nucleotide sequence shown SEQ ID NO:1, or SEQ ID NO:3, or the nucleotide sequence of the cDNA of ATCC 209860.

Also within the invention is a nucleic acid molecule which encodes a fragment of a polypeptide having the amino acid sequence of SEQ ID NO:2, the fragment including at least 15 (25, 30, 50, 100, 150, 300, or 372) contiguous amino acids of SEQ ID NO:2 or the polypeptide encoded by the cDNA of ATCC Accession Number 209860.

The invention includes a nucleic acid molecule which encodes a naturally occurring allelic variant of a polypeptide comprising the amino acid sequence of SEQ ID NO:2 or an amino acid sequence encoded by the cDNA of ATCC Accession Number 209860, wherein the nucleic acid molecule hybridizes to a nucleic acid molecule comprising SEQ ID NO:1 or SEQ ID NO:3 under stringent conditions.

Also within the invention is an isolated AIP-6 protein having an amino acid sequence that is at least about 85%, 95%, or 98% identical to the RING finger domain of SEQ ID NO:2 (e.g., about amino acid residues 324 to 358 of SEQ ID NO:2; SEQ ID NO:4).

Also within the invention are: an isolated AIP-6 protein which is encoded by a nucleic acid molecule having a nucleotide sequence that is at least about 65%, preferably 75%, 85%, or 95% identical to SEQ ID NO:3 or the cDNA of ATCC 209860; an isolated AIP-6 protein which is encoded by a nucleic acid molecule having a nucleotide sequence at least about 65% preferably 75%, 85%, or 95% identical the RING finger domain encoding portion of SEQ ID NO:1 (e.g., about nucleotides 1077 to 1179 of SEQ ID NO:1); and an isolated AIP-6 protein which is encoded by a nucleic acid molecule having a nucleotide sequence which hybridizes under stringent hybridization conditions to a nucleic acid molecule having the nucleotide sequence of SEQ ID NO:3 or the non-coding strand of the cDNA of ATCC 209860.

Also within the invention is a polypeptide which is a naturally occurring allelic variant of a polypeptide that includes the amino acid sequence of SEQ ID NO:2 or an amino acid sequence encoded by the cDNA insert of the plasmid deposited with ATCC as Accession Number 209860, wherein the polypeptide is encoded by a nucleic acid molecule which hybridizes to a nucleic acid molecule comprising SEQ ID NO:1 or SEQ ID NO:3 under stringent conditions.

Another embodiment of the invention features AIP-6 nucleic acid molecules which specifically detect AIP-6 nucleic acid molecules relative to nucleic acid molecules encoding other members of the AIP-6 superfamily. For example, in one embodiment, a AIP-6 nucleic acid molecule hybridizes under stringent conditions to a nucleic acid molecule comprising the nucleotide sequence of SEQ ID NO:1, SEQ ID NO:3, or the cDNA of ATCC 209860, or a complement thereof. In another embodiment, the AIP-6 nucleic acid molecule is at least 300 (325, 350, 375, 400, 425, 450, 500, 550, 600, 650, 700, 800, 900, 1000, 1300, 1600, 1900, 2019, or 2300) nucleotides in length and hybridizes under stringent conditions to a nucleic acid molecule comprising the nucleotide sequence shown in SEQ ID NO:1, SEQ ID NO:3, the cDNA of ATCC 209860, or a complement thereof. In a preferred embodiment, an isolated AIP-6 nucleic acid molecule comprises nucleotides 1077 to 1179 of SEQ ID NO:1, encoding the RING finger domain of AIP-6, or a complement thereof. In another embodiment, the invention provides an isolated nucleic acid molecule which is antisense to the coding strand of a AIP-6 nucleic acid.

Another aspect of the invention provides a vector, e.g., a recombinant expression vector, comprising an AIP-6 nucleic acid molecule of the invention. In another embodiment the invention provides a host cell containing such a vector. The invention also provides a method for producing AIP-6 protein by culturing, in a suitable medium, a host cell of the invention containing a recombinant expression vector such that an AIP-6 protein is produced.

Another aspect of this invention features isolated or recombinant AIP-6 proteins and polypeptides. Preferred AIP-6 proteins and polypeptides possess at least one biological activity possessed by naturally occurring human AIP-6, e.g., (1) the ability to form protein:protein interactions with proteins in the AIP-6 signalling pathway; (2) the ability to bind AIP-6 ligand; (3) the ability to bind to an intracellular target. Other activities include: (1) modulation of cellular proliferation and (2) modulation of cellular differentiation and (3) modulation of cellular death.

The AIP-6 proteins of the present invention, or biologically active portions thereof, can be operatively linked to a non-AIP-6 polypeptide (e.g., heterologous amino acid sequences) to form AIP-6 fusion proteins. The invention further features antibodies that specifically bind AIP-6 proteins, such as monoclonal or polyclonal antibodies. In addition, the AIP-6 proteins or biologically active portions thereof can be incorporated into pharmaceutical compositions, which optionally include pharmaceutically acceptable carriers.

In another aspect, the present invention provides a method for detecting the presence of AIP-6 activity or expression in a biological sample by contacting the biological sample with an agent capable of detecting an indicator of AIP-6 activity such that the presence of AIP-6 activity is detected in the biological sample.

In another aspect, the invention provides a method for modulating AIP-6 activity comprising contacting a cell with an agent that modulates (inhibits or stimulates) AIP-6 activity or expression such that AIP-6 activity or expression in the cell is modulated. In one embodiment, the agent is an antibody that specifically binds to AIP-6 protein. In another embodiment, the agent modulates expression of AIP-6 by modulating transcription of a AIP-6 gene, splicing of a AIP-6 mRNA, or translation of a AIP-6 mRNA. In yet another embodiment, the agent is a nucleic acid molecule having a nucleotide sequence that is antisense to the coding strand of the AIP-6 mRNA or the AIP-6 gene.

In one embodiment, the methods of the present invention are used to treat a subject having a disorder characterized by aberrant AIP-6 protein or nucleic acid expression or activity by administering an agent which is a AIP-6 modulator to the subject. In one embodiment, the AIP-6 modulator is a AIP-6 protein. In another embodiment the AIP-6 modulator is a AIP-6 nucleic acid molecule. In other embodiments, the AIP-6 modulator is a peptide, peptidomimetic, or other small molecule.

AIP-6 may play a role in modulating the apoptotic cell death pathway. AIP-6 function can be altered either by altering the expression of AIP-6 (i.e., altering the amount of AIP-6 present in a given cell at the DNA, mRNA or protein level) or by altering the activity of AIP-6.

Certain disorders are associated with an increased number of surviving cells, which are produced and continue to survive or proliferate when apoptosis is inhibited. These disorders include cancer (particularly follicular lymphomas, carcinomas associated with mutations in p53, and hormone-dependent tumors such as breast cancer, prostate cancer, and ovarian cancer), autoimmune disorders (such as systemic lupus erythematosis, immune-mediated glomerulonephritis), and viral infections (such as those caused by herpesviruses, poxviruses, and adenoviruses). In these cases, patients may be treated with compounds that modulate the expression of AIP-6, or modulate the activity of AIP-6.

Other disorders are associated with excessive lose of cells, e.g., populations of cells are often depleted in the event of viral infection, with perhaps the most dramatic example being the cell depletion caused by the human immunodeficiency virus (HIV). Surprisingly, most T cells that die during HIV infections do not appear to be infected with HIV. Although a number of explanations have been proposed, recent evidence suggests that stimulation of the CD4 receptor results in the enhanced susceptibility of uninfected T cells to undergo apoptosis.

A wide variety of neurological diseases are characterized by the gradual loss of specific sets of neurons. Such disorders include Alzheimer's disease, Parkinson's disease, amyotrophic lateral sclerosis (ALS) retinitis pigmentosa, spinal muscular atrophy, and various forms of cerebellar degeneration. The cell loss in these diseases does not induce an inflammatory response, and apoptosis appears to be the mechanism of cell death.

In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow.

Two common disorders associated with cell death are myocardial infarctions and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis.

The present invention also provides a diagnostic assay for identifying the presence or absence of a genetic lesion or mutation characterized by at least one of: (i) aberrant modification or mutation of a gene encoding a AIP-6 protein; (ii) mis-regulation of a gene encoding a AIP-6 protein; and (iii) aberrant post-translational modification of a AIP-6 protein, wherein a wild-type form of the gene encodes a protein with a AIP-6 activity.

In another aspect, the invention provides a method for identifying a compound that binds to or modulates the activity of a AIP-6 protein. In general, such methods entail measuring a biological activity of a AIP-6 protein in the presence and absence of a test compound and identifying those compounds which alter the activity of the AIP-6 protein.

The invention also features methods for identifying a compound which modulates the expression of AIP-6 by measuring the expression of AIP-6 in the presence and absence of a compound.

Other features and advantages of the invention will be apparent from the following detailed description and claims.

BRIEF DESCRIPTION OF THE DRAWINGS

FIGS. 1A–1B depict the cDNA sequence (SEQ ID NO:1). The open reading frame of SEQ ID NO:1 extends from nucleotide 104 to nucleotide 1219 (SEQ ID NO:3).

FIG. 2 depicts the predicted amino acid sequence (SEQ ID NO:2) of human AIP-6 and the zinc finger domain (SEQ ID NO:4).

DETAILED DESCRIPTION OF THE INVENTION

Figure 3:
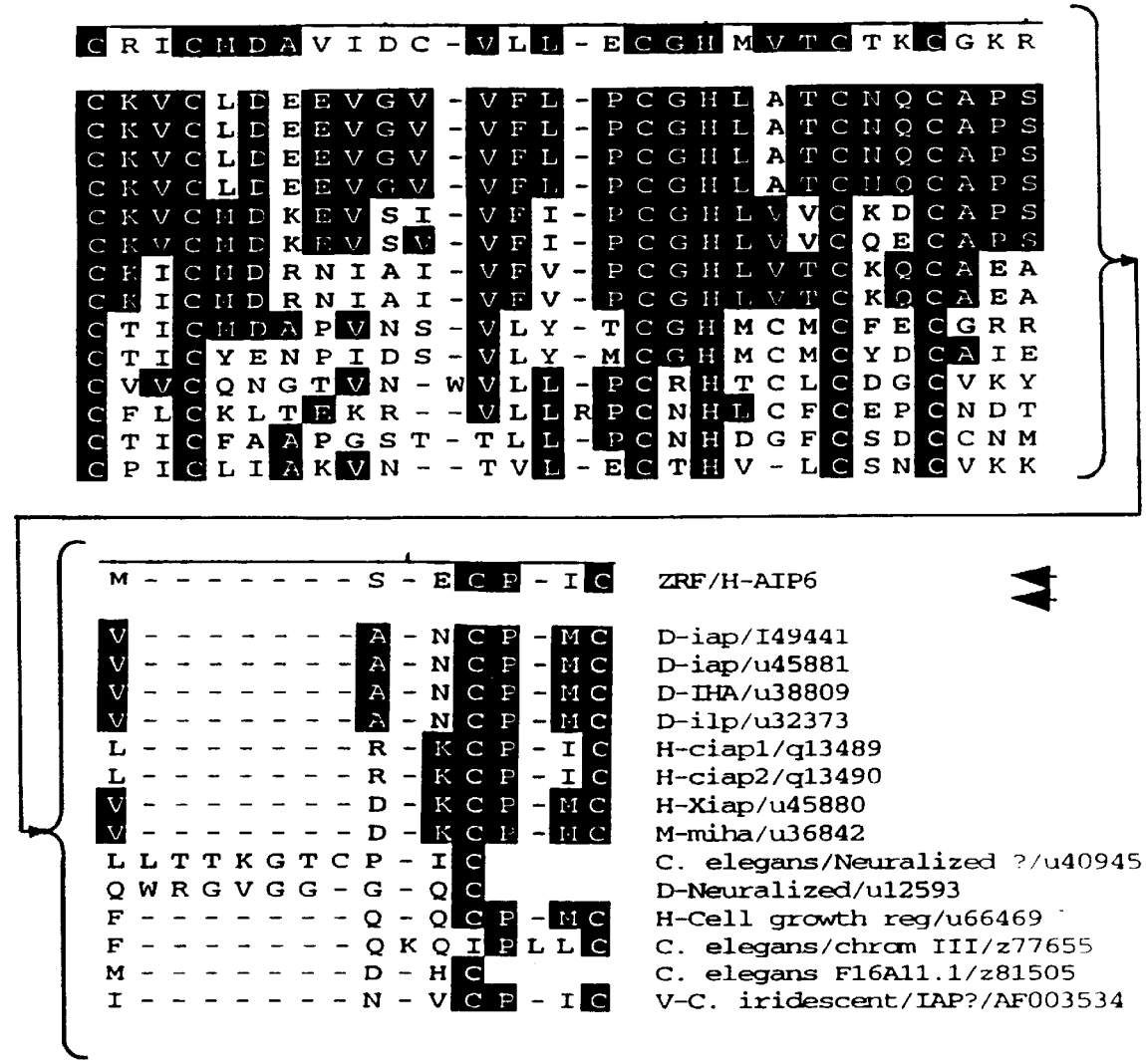
FIG. 3 depicts an alignment of a portion of the amino acid sequence of AIP-6 (SEQ ID NO:4; corresponds to amino acids 324–358 of SEQ ID NO:2) and D-iap (accession number L49441; SEQ ID NO:5), D-iap (accession number u45881; SEQ ID NO:6), D-IHA (accession number u38809; SEQ ID NO:7), D-iap (accession number u32373; SEQ ID NO:8), H-ciap1 (accession number q13489; SEQ ID NO:9), H-ciap2 (accession number q13490; SEQ ID NO:10), H-Xiap (accession number u45880; SEQ ID NO:11), M-miha (accession number u36842; SEQ ID NO:12), C. elegans cosmid (accession number u40945; SEQ ID NO:13), D-Neuralized (accession number u12593; SEQ ID NO:14), H-Cell growth regulator (accession number u66469; SEQ ID NO:15), C. elegans/chrom III (accession number z77655; SEQ ID NO:16), C. elegans F16A11.1 (accession number z81505; SEQ ID NO:17), V-C. iridescent/IAP (accession number AF003534; SEQ ID NO:18).

The present invention is based on the discovery of a cDNA molecule encoding human AIP-6, a member of the AIP-6 superfamily. A nucleotide sequence encoding a human AIP-6 protein is shown in FIGS. 1A–1B (SEQ ID NO:1; SEQ ID NO:3 includes the open reading frame only). A predicted amino acid sequence of AIP-6 protein is shown in FIG. 2 (SEQ ID NO: 2).

The AIP-6 cDNA of FIGS. 1A–1B (SEQ ID NO:1), which is approximately 2026 nucleotides long including untranslated regions, encodes a protein amino acid having a molecular weight of approximately 42 kDa (excluding post-translational modifications). A plasmid containing a cDNA encoding human AIP-6 was deposited with American Type Culture Collection (ATCC), 1801 University Boulevard, Manassas, Va. 20110-2209, on May 13, 1998, and assigned Accession Number 209860. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

An approximately 2.2 kb AIP-6 mRNA transcript is constitutively expressed at a low level in spleen, thymus, prostate, ovary, and small intestine colon. Moderate levels of this transcript were observed in testis, and none was expressed in peripheral blood leukocytes.

Expression of AIP-6 was shown to be low in cancer cell line Burkitt lymphoma Raji, moderately expressed in melanoma G361 and highly expressed in promyelocyte leukemia HL-60, hela Cell S3, chronic myelogenous leukemia K-562, lymphoblastic leukemia Molt-4, colorectal adenocarcinoma SW480 and lung carcinoma SW480.

Human AIP-6 is one member of a family of molecules (the "AIP-6 family") having certain conserved structural and functional features. The term "family" when referring to the protein and nucleic acid molecules of the invention is intended to mean two or more proteins or nucleic acid molecules having a common structural domain and having sufficient amino acid or nucleotide sequence identity as defined herein. Such family members can be naturally occurring and can be from either the same or different species. For example, a family can contain a first protein of human origin and a homologue of that protein of murine origin, as well as a second, distinct protein of human origin and a murine homologue of that protein. Members of a family may also have common functional characteristics.

In one embodiment, a AIP-6 protein includes a RING finger domain having at least about 65%, preferably at least about 75%, and more preferably about 85%, 95%, or 98% amino acid sequence identity to the RING finger domain of SEQ ID NO:4.

Preferred AIP-6 polypeptides of the present invention have an amino acid sequence sufficiently identical to the RING finger domain of SEQ ID NO:4. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences have a common structural domain and/or common functional activity. For example, amino acid or nucleotide sequences which contain a common structural domain having about 65% identity, preferably 75% identity, more preferably 85%, 95%, or 98% identity are defined herein as sufficiently identical.

As used interchangeably herein a "AIP-6 activity", "biological activity of AIP-6" or "functional activity of AIP-6", refers to an activity exerted by a AIP-6 protein, polypeptide or nucleic acid molecule on a AIP-6 responsive cell as determined in vivo, or in vitro, according to standard techniques. AIP-6 activity can be a direct activity, such as an association with or an enzymatic activity on a second protein or an indirect activity, such as a cellular signaling activity mediated by interaction of the AIP-6 protein with a second protein. In a preferred embodiment, a AIP-6 activity includes at least one or more of the following activities: (i) interaction with proteins in the apoptotic signalling pathway (ii) interaction with a AIP-6 ligand; or (iii) interaction with an intracellular target protein.

Accordingly, another embodiment of the invention features isolated AIP-6 proteins and polypeptides having a AIP-6 activity. Various aspects of the invention are described in further detail in the following subsections.

I. Isolated Nucleic Acid Molecules

One aspect of the invention pertains to isolated nucleic acid molecules that encode AIP-6 proteins or biologically active portions thereof, as well as nucleic acid molecules sufficient for use as hybridization probes to identify AIP-6-encoding nucleic acids (e.g., AIP-6 mRNA) and fragments for use as PCR primers for the amplification or mutation of AIP-6 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences (preferably protein encoding sequences) which naturally flank the nucleic acid (i.e., sequences located at the 5' and 3' ends of the nucleic acid) in the genomic DNA of the organism from which the nucleic acid is derived. For example, in various embodiments, the isolated AIP-6 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, SEQ ID NO:3, or the cDNA of ATCC 209860, or a complement of any of these nucleotide sequences, can be isolated using standard molecular biology techniques and the sequence information provided herein. Using all or portion of the nucleic acid sequences of SEQ ID NO:1, SEQ ID NO:3, or the cDNA of ATCC 209860 as a hybridization probe, AIP-6 nucleic acid molecules can be isolated using standard hybridization and cloning techniques (e.g., as described in Sambrook et al., eds., *Molecular Cloning: A Laboratory Manual. 2nd, ed., Cold Spring Harbor Laboratory*, Cold Spring Harbor Laboratory Press, Cold Spring Harbor, N.Y., 1989).

A nucleic acid of the invention can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to AIP-6 nucleotide sequences can be prepared by standard synthetic techniques, e.g., using an automated DNA synthesizer.

In another preferred embodiment, an isolated nucleic acid molecule of the invention comprises a nucleic acid molecule which is a complement of the nucleotide sequence shown in SEQ ID NO:1, SEQ ID NO:3, or the cDNA of ATCC 209860, or a portion thereof. A nucleic acid molecule which is complementary to a given nucleotide sequence is one which is sufficiently complementary to the given nucleotide sequence that it can hybridize to the given nucleotide sequence thereby forming a stable duplex.

Moreover, the nucleic acid molecule of the invention can comprise only a portion of a nucleic acid sequence encoding AIP-6, for example, a fragment which can be used as a probe or primer or a fragment encoding a biologically active portion of AIP-6. The nucleotide sequence determined from the cloning of the human AIP-6 gene allows for the generation of probes and primers designed for use in identifying and/or cloning AIP-6 homologues in other cell types, e.g., from other tissues, as well as AIP-6 homologues from other mammals. The probe/primer typically comprises substantially purified oligonucleotide. The oligonucleotide typically comprises a region of nucleotide sequence that hybridizes under stringent conditions to at least about 12, preferably about 25, more preferably about 50, 75, 100, 125, 150, 175, 200, 250, 300, 350 or 400 consecutive nucleotides of the sense or anti-sense sequence of SEQ ID NO:1, SEQ ID NO:3, or the cDNA of ATCC 209860 or of a naturally occurring mutant of SEQ ID NO:1, SEQ ID NO:3, or the cDNA of ATCC 209860.

Probes based on the human AIP-6 nucleotide sequence can be used to detect transcripts or genomic sequences encoding the same or identical proteins. The probe comprises a label group attached thereto, e.g., a radioisotope, a fluorescent compound, an enzyme, or an enzyme co-factor. Such probes can be used as a part of a diagnostic test kit for identifying cells or tissue which mis-express a AIP-6 protein, such as by measuring a level of a AIP-6-encoding nucleic acid in a sample of cells from a subject, e.g., detecting AIP-6 mRNA levels or determining whether a genomic AIP-6 gene has been mutated or deleted.

A nucleic acid fragment encoding a "biologically active portion of AIP-6" can be prepared by isolating a portion of SEQ ID NO:1, SEQ ID NO:3, or the nucleotide sequence of the cDNA of ATCC 209860 which encodes a polypeptide having a AIP-6 biological activity, expressing the encoded portion of AIP-6 protein (e.g., by recombinant expression in vitro) and assessing the activity of the encoded portion of AIP-6. For example, a nucleic acid fragment encoding a biologically active portion of AIP-6 includes a RING finger domain, e.g., SEQ ID NO:4.

The invention further encompasses nucleic acid molecules that differ from the nucleotide sequence of SEQ ID NO:1, SEQ ID NO:3, or the cDNA of ATCC 209860 due to degeneracy of the genetic code and thus encode the same AIP-6 protein as that encoded by the nucleotide sequence shown in SEQ ID NO:1, SEQ ID NO:3, or the cDNA of ATCC 209860.

In addition to the human AIP-6 nucleotide sequence shown in SEQ ID NO:1, SEQ ID NO:3, or the cDNA of ATCC 209860, it will be appreciated by those skilled in the art that DNA sequence polymorphisms that lead to changes in the amino acid sequences of AIP-6 may exist within a population (e.g., the human population). Such genetic polymorphism in the AIP-6 gene may exist among individuals within a population due to natural allelic variation. As used herein, the terms "gene" and "recombinant gene" refer to nucleic acid molecules comprising an open reading frame encoding a AIP-6 protein, preferably a mammalian AIP-6 protein. Such natural allelic variations can typically result in 1–5% variance in the nucleotide sequence of the AIP-6 gene. Any and all such nucleotide variations and resulting amino acid polymorphisms in AIP-6 that are the result of natural allelic variation and that do not alter the functional activity of AIP-6 are intended to be within the scope of the invention.

Moreover, nucleic acid molecules encoding AIP-6 proteins from other species (AIP-6 homologues), which have a nucleotide sequence which differs from that of a human AIP-6, are intended to be within the scope of the invention. Nucleic acid molecules corresponding to natural allelic variants and homologues of the AIP-6 cDNA of the invention can be isolated based on their identity to the human AIP-6 nucleic acids disclosed herein using the human cDNAs, or a portion thereof, as a hybridization probe according to standard hybridization techniques under stringent hybridization conditions.

Accordingly, in another embodiment, an isolated nucleic acid molecule of the invention is at least 300 (325, 350, 375, 400, 425, 450, 500, 550, 600, 650, 700, 800, 900, 1000, or 1290) nucleotides in length and hybridizes under stringent conditions to the nucleic acid molecule comprising the nucleotide sequence, preferably the coding sequence, of SEQ ID NO:1, SEQ ID NO:3, or the cDNA of ATCC 209860.

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in Current Protocols in Molecular Biology, John Wiley & Sons, N.Y. (1989), 6.3.1–6.3.6. A preferred, non-limiting example of stringent hybridization conditions are hybridization in 6× sodium chloride/sodium citrate (SSC) at about 45° C, followed by one or more washes in 0.2×SSC, 0.1% SDS at 50–65° C. Preferably, an isolated nucleic acid molecule of the invention that hybridizes under stringent conditions to the sequence of SEQ ID NO:1, SEQ ID NO:3, the cDNA of ATCC 209860 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the AIP-6 sequence that may exist in the population, the skilled artisan will further appreciate that changes can be introduced by mutation into the nucleotide sequence of SEQ ID NO:1, SEQ ID NO:3, the cDNA of ATCC 209860, thereby leading to changes in the amino acid sequence of the encoded AIP-6 protein, without altering the functional ability of the AIP-6 protein. For example, one can make nucleotide substitutions leading to amino acid substitutions at "non-essential" amino acid residues. A "non-essential" amino acid residue is a residue that can be altered from the wild-type sequence of AIP-6 (e.g., the sequence of SEQ ID NO:2) without altering the biological activity, whereas an "essential" amino acid residue is required for biological activity. For example, amino acid residues that are conserved among the AIP-6 proteins of various species are predicted to be particularly unamenable to alteration.

For example, preferred AIP-6 proteins of the present invention, contain at least one Ring finger domain. Other amino acid residues, however, (e.g., those that are not conserved or only semi-conserved among AIP-6 of various species) may not be essential for activity and thus are likely to be amenable to alteration.

Accordingly, another aspect of the invention pertains to nucleic acid molecules encoding AIP-6 proteins that contain changes in amino acid residues that are not essential for activity. Such AIP-6 proteins differ in amino acid sequence from SEQ ID NO:2 yet retain biological activity. In one embodiment, the isolated nucleic acid molecule includes a nucleotide sequence encoding a protein that includes an amino acid sequence that is at least about 45% identical, 65%, 75%, 85%, 95%, or 98% identical to the amino acid sequence of SEQ ID NO:2.

An isolated nucleic acid molecule encoding a AIP-6 protein having a sequence which differs from that of SEQ ID NO:2 can be created by introducing one or more nucleotide substitutions, additions or deletions into the nucleotide sequence of SEQ ID NO:1, SEQ ID NO:3, the cDNA of ATCC 209860 such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in AIP-6 is preferably replaced with another amino acid residue from the same side chain family. Alternatively, mutations can be introduced randomly along all or part of a AIP-6 coding sequence, such as by saturation mutagenesis, and the resultant mutants can be screened for AIP-6 biological activity to identify mutants that retain activity. Following mutagenesis, the encoded protein can be expressed recombinantly and the activity of the protein can be determined.

In a preferred embodiment, a mutant AIP-6 protein can be assayed for: (1) the ability to form protein:protein interactions with proteins in the apoptotoic signalling pathway; (2) the ability to bind a AIP-6 ligand; or (3) the ability to bind to an intracellular target protein. In yet another preferred embodiment, a mutant AIP-6 can be assayed for the ability to modulate cellular proliferation, cellular differentiation and cellular death.

The present invention encompasses antisense nucleic acid molecules, i.e., molecules which are complementary to a sense nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire AIP-6 coding strand, or to only a portion thereof, e.g., all or part of the protein coding region (or open reading frame). An antisense nucleic acid molecule can be antisense to a noncoding region of the coding strand of a nucleotide sequence encoding AIP-6. The noncoding regions ("5' and 3' untranslated regions") are the 5' and 3' sequences which flank the coding region and are not translated into amino acids.

Given the coding strand sequences encoding AIP-6 disclosed herein (e.g., SEQ ID NO:1 or SEQ ID NO:3), antisense nucleic acids of the invention can be designed according to the rules of Watson and Crick base pairing. The antisense nucleic acid molecule can be complementary to the entire coding region of AIP-6 mRNA, but more preferably is an oligonucleotide which is antisense to only a portion of the coding or noncoding region of AIP-6 mRNA. For example, the antisense oligonucleotide can be complementary to the region surrounding the translation start site of AIP-6 mRNA, e.g., an oligonucleotide having the sequence ACTCCGCCAGCGCCGGTAGTT (SEQ ID NO:19) or GCGCCGGTAGTTCCGCCCACG (SEQ ID NO:20). An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a AIP-6 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave AIP-6 mRNA transcripts to thereby inhibit translation of AIP-6 mRNA. A ribozyme having specificity for a AIP-6-encoding nucleic acid can be designed based upon the nucleotide sequence of a AIP-6 cDNA disclosed herein (e.g., SEQ ID NO:1, SEQ ID NO:3). For example, a derivative of a Tetrahymena L-19 IVS RNA can be constructed in which the nucleotide sequence of the active site is complementary to the nucleotide sequence to be cleaved in a AIP-6-encoding mRNA. See, e.g., Cech et al. U.S. Pat. No. 4,987,071; and Cech et al. U.S. Pat. No. 5,116,742. Alternatively, AIP-6 mRNA can be used to select a catalytic RNA having a specific ribonuclease activity from a pool of RNA molecules. See, e.g., Bartel and Szostak (1993) *Science* 261:1411–1418.

The invention also encompasses nucleic acid molecules which form triple helical structures. For example, AIP-6 gene expression can be inhibited by targeting nucleotide sequences complementary to the regulatory region of the AIP-6 (e.g., the AIP-6 promoter and/or enhancers) to form triple helical structures that prevent transcription of the AIP-6 gene in target cells. See generally, Helene (1991) *Anticancer Drug Des.* 6(6):569–84; Helene (1992) *Ann. N.Y. Acad. Sci.* 660:27–36; and Maher (1992) *Bioassays* 14(12):807–15.

In preferred embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4(1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) supra; Perry-O'Keefe et al. (1996) *Proc. Natl. Acad. Sci. USA* 93: 14670–675.

PNAs of AIP-6 can be used therapeutic and diagnostic applications. For example, PNAs can be used as antisense or antigene agents for sequence-specific modulation of gene expression by, e.g., inducing transcription or translation arrest or inhibiting replication. PNAs of AIP-6 can also be used, e.g., in the analysis of single base pair mutations in a gene by, e.g., PNA directed PCR clamping; as 'artificial restriction enzymes when used in combination with other enzymes, e.g., S1 nucleases (Hyrup (1996) supra; or as probes or primers for DNA sequence and hybridization (Hyrup (1996) supra; Perry-O'Keefe et al. (1996) *Proc. Natl. Acad. Sci. USA* 93: 14670–675).

In another embodiment, PNAs of AIP-6 can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of AIP-6 can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) supra). The synthesis of PNA-DNA chimeras can be performed as described in Hyrup (1996) supra and Finn et al. (1996) *Nucleic Acids Research* 24(17):3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag et al. (1989) *Nucleic Acid Res.* 17:5973–88). PNA monomers are then coupled in a stepwise manner to produce a chimeric molecule with a 5' PNA segment and a 3' DNA segment (Finn et al. (1996) *Nucleic Acids Research* 24(17):3357–63). Alternatively, chimeric molecules can be synthesized with a 5' DNA segment and a 3' PNA segment (Peterser et al. (1975) *Bioorganic Med. Chem. Lett.* 5:1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) *Bio/Techniques* 6:958–976) or intercalating agents (see, e.g., Zon (1988) *Pharm. Res.* 5:539–549). To this end, the oligonucleotide may be conjugated to another molecule, e.g., a peptide, hybridization triggered cross-linking agent, transport agent, hybridization-triggered cleavage agent, etc.

II. Isolated AIP-6 Proteins and Anti-AIP-6 Antibodies

One aspect of the invention pertains to isolated AIP-6 proteins, and biologically active portions thereof, as well as polypeptide fragments suitable for use as immunogens to raise anti-AIP-6 antibodies. In one embodiment, native AIP-6 proteins can be isolated from cells or tissue sources by an appropriate purification scheme using standard protein purification techniques. In another embodiment, AIP-6 proteins are produced by recombinant DNA techniques. Alternative to recombinant expression, a AIP-6 protein or polypeptide can be synthesized chemically using standard peptide synthesis techniques.

An "isolated" or "purified" protein or biologically active portion thereof is substantially free of cellular material or other contaminating proteins from the cell or tissue source from which the AIP-6 protein is derived, or substantially free from chemical precursors or other chemicals when chemically synthesized. The language "substantially free of cellular material" includes preparations of AIP-6 protein in which the protein is separated from cellular components of the cells from which it is isolated or recombinantly produced. Thus, AIP-6 protein that is substantially free of cellular material includes preparations of AIP-6 protein having less than about 30%, 20%, 10%, or 5% (by dry weight) of non-AIP-6 protein (also referred to herein as a "contaminating protein"). When the AIP-6 protein or biologically active portion thereof is recombinantly produced, it is also preferably substantially free of culture medium, i.e., culture medium represents less than about 20%, 10%, or 5% of the volume of the protein preparation. When AIP-6 protein is produced by chemical synthesis, it is preferably substantially free of chemical precursors or other chemicals, i.e., it is separated from chemical precursors or other chemicals which are involved in the synthesis of the protein. Accordingly such preparations of AIP-6 protein have less than about 30%, 20%, 10%, 5% (by dry weight) of chemical precursors or non-AIP-6 chemicals. Biologically active portions of a AIP-6 protein include peptides comprising amino acid sequences sufficiently identical to or derived from the amino acid sequence of the AIP-6 protein (e.g., the amino acid sequence shown in SEQ ID NO:2 or SEQ ID NO:4), which include less amino acids than the full length AIP-6 proteins, and exhibit at least one activity of a AIP-6 protein. Typically, biologically active portions comprise a domain or domain with at least one activity of the AIP-6 protein. A biologically active portion of a AIP-6 protein can be a polypeptide which is, for example, 10, 25, 50, 100 or more amino acids in length. Preferred biologically active polypeptides include one or more identified AIP-6 structural domains, e.g., the RING finger domain (SEQ ID NO:4).

Moreover, other biologically active portions, in which other regions of the protein are deleted, can be prepared by recombinant techniques and evaluated for one or more of the functional activities of a native AIP-6 protein.

Preferred AIP-6 protein has the amino acid sequence shown of SEQ ID NO:2. Other useful AIP-6 proteins are substantially identical to SEQ ID NO:2 and retain the functional activity of the protein of SEQ ID NO:2 yet differ in amino acid sequence due to natural allelic variation or mutagenesis. AIP-6 may play a role in modulating apoptotic cell death. Accordingly, a useful AIP-6 protein is a protein which includes an amino acid sequence at least about 45%, preferably 55%, 65%, 75%, 85%, 95%, or 99% identical to the amino acid sequence of SEQ ID NO:2 and retains the functional activity of the AIP-6 proteins of SEQ ID NO:2. In other instances, the AIP-6 protein is a protein having an amino acid sequence 55%, 65%, 75%, 85%, 95%, or 98% identical to the AIP-6 RING finger domain (SEQ ID NO:4). In a preferred embodiment, the AIP-6 protein retains a functional activity of the AIP-6 protein of SEQ ID NO:2.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions× 100).

The determination of percent homology between two sequences can be accomplished using a mathematical algorithm. A preferred, non-limiting example of a mathematical algorithm utilized for the comparison of two sequences is the algorithm of Karlin and Altschul (1990) Proc. Nat'l Acad. Sci. USA 87:2264–2268, modified as in Karlin and Altschul (1993) Proc. Nat'l Acad. Sci. USA 90:5873–5877. Such an algorithm is incorporated into the NBLAST and XBLAST programs of Altschul, et al. (1990) J. Mol. Biol. 215:403–410. BLAST nucleotide searches can be performed with the NBLAST program, score=100, wordlength=12 to obtain nucleotide sequences homologous to AIP-6 nucleic acid molecules of the invention. BLAST protein searches can be performed with the XBLAST program, score=50, wordlength=3 to obtain amino acid sequences homologous to AIP-6 protein molecules of the invention. To obtain gapped alignments for comparison purposes, Gapped BLAST can be utilized as described in Altschul et al., (1997) Nucleic Acids Res. 25:3389–3402. When utilizing BLAST and Gapped BLAST programs, the default parameters of the respective programs (e.g., XBLAST and NBLAST) can be used. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, only exact matches are counted.

The invention also provides AIP-6 chimeric or fusion proteins. As used herein, a AIP-6 "chimeric protein" or "fusion protein" comprises a AIP-6 polypeptide operatively linked to a non-AIP-6 polypeptide. A "AIP-6 polypeptide" refers to a polypeptide having an amino acid sequence corresponding to AIP-6, whereas a "non-AIP-6 polypeptide" refers to a polypeptide having an amino acid sequence corresponding to a protein which is not substantially identical to the AIP-6 protein, e.g., a protein which is different from the AIP-6 protein and which is derived from the same or a different organism. Within a AIP-6 fusion protein the AIP-6 polypeptide can correspond to all or a portion of a AIP-6 protein, preferably at least one biologically active portion of a AIP-6 protein. Within the fusion protein, the term "operatively linked" is intended to indicate that the AIP-6 polypeptide and the non-AIP-6 polypeptide are fused in-frame to each other. The non-AIP-6 polypeptide can be fused to the N-terminus or C-terminus of the AIP-6 polypeptide.

One useful fusion protein is a GST-AIP-6 fusion protein in which the AIP-6 sequences are fused to the C-terminus of the GST sequences. Such fusion proteins can facilitate the purification of recombinant AIP-6.

In another embodiment, the fusion protein is a AIP-6 protein containing a heterologous signal sequence at its N-terminus. In certain host cells (e.g., mammalian host cells), expression and/or secretion of AIP-6 can be increased through use of a heterologous signal sequence. For example, the gp67 secretory sequence of the baculovirus envelope protein can be used as a heterologous signal sequence (*Current Protocols in Molecular Biology*, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (*Molecular cloning*, Sambrook et al, second edition, Cold spring harbor laboratory press, 1989) and the protein A secretory signal (Pharmacia Biotech; Piscataway, N.J.).

In yet another embodiment, the fusion protein is an AIP-6-immunoglobulin fusion protein in which all or part of AIP-6 is fused to sequences derived from a member of the immunoglobulin protein family. The AIP-6-immunoglobulin fusion proteins of the invention can be incorporated into pharmaceutical compositions and administered to a subject. The AIP-6-immunoglobulin fusion proteins can be used to affect the bioavailability of a AIP-6 cognate ligand. Inhibition of the AIP-6 ligand/AIP-6 interaction may be useful therapeutically for both the treatment of proliferative and differentiative disorders, as well as modulating (e.g. promoting or inhibiting) cell survival. Moreover, the AIP-6-immunoglobulin fusion proteins of the invention can be used as immunogens to produce anti-AIP-6 antibodies in a subject, to purify AIP-6 ligands and in screening assays to identify molecules which inhibit the interaction of AIP-6 with a AIP-6 ligand.

Preferably, a AIP-6 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., *Current Protocols in Molecular Biology*, Ausubel et al. eds., John Wiley & Sons: 1992). Moreover, many expression vectors are commercially available that already encode a fusion moiety (e.g., a GST polypeptide). An AIP-6-encoding nucleic acid can be cloned into such an expression vector such that the fusion moiety is linked in-frame to the AIP-6 protein.

The present invention also pertains to variants of the AIP-6 proteins which function as either AIP-6 agonists (mimetics) or as AIP-6 antagonists. Variants of the AIP-6 protein can be generated by mutagenesis, e.g., discrete point mutation or truncation of the AIP-6 protein. An agonist of the AIP-6 protein can retain substantially the same, or a subset, of the biological activities of the naturally occurring form of the AIP-6 protein. An antagonist of the AIP-6 protein can inhibit one or more of the activities of the naturally occurring form of the AIP-6 protein by, for example, competitively binding to a downstream or upstream member of a cellular signaling cascade which includes the AIP-6 protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the AIP-6 proteins.

Variants of the AIP-6 protein which function as either AIP-6 agonists (mimetics) or as AIP-6 antagonists can be identified by screening combinatorial libraries of mutants, e.g., truncation mutants, of the AIP-6 protein for AIP-6 protein agonist or antagonist activity. In one embodiment, a variegated library of AIP-6 variants is generated by combinatorial mutagenesis at the nucleic acid level and is encoded by a variegated gene library. A variegated library of AIP-6 variants can be produced by, for example, enzymatically ligating a mixture of synthetic oligonucleotides into gene sequences such that a degenerate set of potential AIP-6 sequences is expressible as individual polypeptides, or alternatively, as a set of larger fusion proteins (e.g., for phage display) containing the set of AIP-6 sequences therein. There are a variety of methods which can be used to produce libraries of potential AIP-6 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential AIP-6 sequences. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of the AIP-6 protein coding sequence can be used to generate a variegated population of AIP-6 fragments for screening and subsequent selection of variants of a AIP-6 protein. In one embodiment, a library of coding sequence fragments can be generated by treating a double stranded PCR fragment of a AIP-6 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the AIP-6 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of AIP-6 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify AIP-6 variants (Arkin and Yourvan (1992) *Proc. Natl. Acad. Sci. USA* 89:7811–7815; Delgrave et al. (1993) *Protein Engineering* 6(3):327–331).

An isolated AIP-6 protein, or a portion or fragment thereof, can be used as an immunogen to generate antibodies that bind AIP-6 using standard techniques for polyclonal and monoclonal antibody preparation. The full-length AIP-6 protein can be used or, alternatively, the invention provides antigenic peptide fragments of AIP-6 for use as immunogens. The antigenic peptide of AIP-6 comprises at least 8 (preferably 10, 15, 20, or 30) amino acid residues of the amino acid sequence shown in SEQ ID NO:2 and encompasses an epitope of AIP-6 such that an antibody raised against the peptide forms a specific immune complex with AIP-6.

Preferred epitopes encompassed by the antigenic peptide are regions of AIP-6 that are located on the surface of the protein, e.g., hydrophilic regions.

A AIP-6 immunogen typically is used to prepare antibodies by immunizing a suitable subject, (e.g., rabbit, goat, mouse or other mammal) with the immunogen. An appropriate immunogenic preparation can contain, for example, recombinantly expressed AIP-6 protein or a chemically synthesized AIP-6 polypeptide. The preparation can further include an adjuvant, such as Freund's complete or incomplete adjuvant, or similar immunostimulatory agent. Immunization of a suitable subject with an immunogenic AIP-6 preparation induces a polyclonal anti-AIP-6 antibody response.

Accordingly, another aspect of the invention pertains to anti-AIP-6 antibodies. The term "antibody" as used herein refers to immunoglobulin molecules and immunologically active portions of immunoglobulin molecules, i.e., molecules that contain an antigen binding site which specifically binds an antigen, such as AIP-6. A molecule which specifically binds to AIP-6 is a molecule which binds AIP-6, but does not substantially bind other molecules in a sample, e.g., a biological sample, which naturally contains AIP-6. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind AIP-6. The term "monoclonal antibody" or "monoclonal antibody composition", as used herein, refers to a population of antibody molecules that contain only one species of an antigen binding site capable of immunoreacting with a particular epitope of AIP-6. A monoclonal antibody composition thus typically displays a single binding affinity for a particular AIP-6 protein with which it immunoreacts.

Polyclonal anti-AIP-6 antibodies can be prepared as described above by immunizing a suitable subject with a AIP-6 immunogen. The anti-AIP-6 antibody titer in the immunized subject can be monitored over time by standard techniques, such as with an enzyme linked immunosorbent assay (ELISA) using immobilized AIP-6. If desired, the antibody molecules directed against AIP-6 can be isolated from the mammal (e.g., from the blood) and further purified by well-known techniques, such as protein A chromatography to obtain the IgG fraction. At an appropriate time after immunization, e.g., when the anti-AIP-6 antibody titers are highest, antibody-producing cells can be obtained from the subject and used to prepare monoclonal antibodies by standard techniques, such as the hybridoma technique originally described by Kohler and Milstein (1975) *Nature* 256:495–497, the human B cell hybridoma technique (Kozbor et al. (1983) *Immunol Today* 4:72), the EBV-hybridoma technique (Cole et al. (1985), Monoclonal Antibodies and Cancer Therapy, Alan R. Liss, Inc., pp. 77–96) or trioma techniques. The technology for producing various antibodies monoclonal antibody hybridomas is well known (see generally Current Protocols in Immunology (1994) Coligan et al. (eds.) John Wiley & Sons, Inc., New York, N.Y.). Briefly, an immortal cell line (typically a myeloma) is fused to lymphocytes (typically splenocytes) from a mammal immunized with a AIP-6 immunogen as described above, and the culture supernatants of the resulting hybridoma cells are screened to identify a hybridoma producing a monoclonal antibody that binds AIP-6.

Any of the many well known protocols used for fusing lymphocytes and immortalized cell lines can be applied for the purpose of generating an anti-AIP-6 monoclonal antibody (see, e.g., Current Protocols in Immunology, supra; Galfre et al. (1977) *Nature* 266:55052; R. H. Kenneth, in *Monoclonal Antibodies: A New Dimension In Biological Analyses*, Plenum Publishing Corp., New York, N.Y. (1980); and Lerner (1981) *Yale J. Biol. Med.*, 54:387–402. Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line, e.g., a myeloma cell line that is sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind AIP-6, e.g., using a standard ELISA assay.

Alternative to preparing monoclonal antibody-secreting hybridomas, a monoclonal anti-AIP-6 antibody can be identified and isolated by screening a recombinant combinatorial immunoglobulin library (e.g., an antibody phage display library) with AIP-6 to thereby isolate immunoglobulin library members that bind AIP-6. Kits for generating and screening phage display libraries are commercially available (e.g., the Pharmacia *Recombinant Phage Antibody System*, Catalog No. 27-9400-01; and the Stratagene *SurfZAP*™ *Phage Display Kit*, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734.

Additionally, recombinant anti-AIP-6 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, (1985) *Science* 229:1202–1207; Oi et al. (1986) *Bio/Techniques* 4:214; U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

An anti-AIP-6 antibody (e.g., monoclonal antibody) can be used to isolate AIP-6 by standard techniques, such as affinity chromatography or immunoprecipitation. An anti-AIP-6 antibody can facilitate the purification of natural AIP-6 from cells and of recombinantly produced AIP-6 expressed in host cells. Moreover, an anti-AIP-6 antibody can be used to detect AIP-6 protein (e.g., in a cellular lysate) in order to evaluate the abundance and pattern of expression of the AIP-6 protein. Anti-AIP-6 antibodies can be used diagnostically to monitor protein levels in tissue as part of a clinical testing procedure, e.g., to determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Another aspect of the invention pertains to vectors, preferably expression vectors, containing a nucleic acid encoding AIP-6 (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operatively linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., AIP-6 proteins, mutant forms of AIP-6, fusion proteins, etc.).

The recombinant expression vectors of the invention can be designed for expression of AIP-6 in prokaryotic or eukaryotic cells, e.g., bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111–2118). Such alteration of nucleic acid sequences of the invention can be carried out by standard DNA synthesis techniques.

In another embodiment, the AIP-6 expression vector is a yeast expression vector. Examples of vectors for expression in yeast *S. cerivisae* include pYepSec1 (Baldari et al. (1987) *EMBO J*. 6:229–234), pMFa (Kurjan and Herskowitz, (1982) *Cell* 30:933–943), pJRY88 (Schultz et al. (1987) *Gene* 54:113–123), pYES2 (Invitrogen Corporation, San Diego, Calif.), and picZ (InVitrogen Corp, San Diego, Calif.).

Alternatively, AIP-6 can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al. (supra).

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to AIP-6 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (*Reviews—Trends in Genetics*, Vol. 1(1) 1986).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, AIP-6 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding AIP-6 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) AIP-6 protein. Accordingly, the invention further provides methods for producing AIP-6 protein using the host cells of the invention. In one embodiment, the method comprises culturing the host cell of invention (into which a recombinant expression vector encoding AIP-6 has been introduced) in a suitable medium such that AIP-6 protein is produced. In another embodiment, the method further comprises isolating AIP-6 from the medium or the host cell.

The host cells of the invention can also be used to produce nonhuman transgenic animals. For example, in one embodiment, a host cell of the invention is a fertilized oocyte or an embryonic stem cell into which AIP-6-coding sequences have been introduced. Such host cells can then be used to create non-human transgenic animals in which exogenous AIP-6 sequences have been introduced into their genome or homologous recombinant animals in which endogenous AIP-6 sequences have been altered. Such animals are useful for studying the function and/or activity of AIP-6 and for identifying and/or evaluating modulators of AIP-6 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous AIP-6 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing AIP-6-encoding nucleic acid into the male pronuclei of a fertilized oocyte, e.g., by microinjection, retroviral infection, and allowing the oocyte to develop in a pseudopregnant female foster animal. The AIP-6 cDNA sequence e.g., that of (SEQ ID NO:1, SEQ ID NO:3, or the cDNA of ATCC 209860) can be introduced as a transgene into the genome of a non-human animal. Alternatively, a nonhuman homologue of the human AIP-6 gene, such as a mouse AIP-6 gene, can be isolated based on hybridization to the human AIP-6 cDNA and used as a transgene. Intronic sequences and polyadenylation signals can also be included in the transgene to increase the efficiency of expression of the transgene. A tissue-specific regulatory sequence(s) can be operably linked to the AIP-6 transgene to direct expression of AIP-6 protein to particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of the AIP-6 transgene in its genome and/or expression of AIP-6 mRNA in tissues or cells of the animals. A transgenic founder animal can then be used to breed additional animals carrying the transgene. Moreover, transgenic animals carrying a transgene encoding AIP-6 can further be bred to other transgenic animals carrying other transgenes.

To create an homologous recombinant animal, a vector is prepared which contains at least a portion of a AIP-6 gene (e.g., a human or a non-human homolog of the AIP-6 gene, e.g., a murine AIP-6 gene) into which a deletion, addition or substitution has been introduced to thereby alter, e.g., functionally disrupt, the AIP-6 gene. In a preferred embodiment, the vector is designed such that, upon homologous recombination, the endogenous AIP-6 gene is functionally disrupted (i.e., no longer encodes a functional protein; also referred to as a "knock out" vector). Alternatively, the vector can be designed such that, upon homologous recombination, the endogenous AIP-6 gene is mutated or otherwise altered but still encodes functional protein (e.g., the upstream regulatory region can be altered to thereby alter the expression of the endogenous AIP-6 protein). In the homologous recombination vector, the altered portion of the AIP-6 gene is flanked at its 5' and 3' ends by additional nucleic acid of the AIP-6 gene to allow for homologous recombination to occur between the exogenous AIP-6 gene carried by the vector and an endogenous AIP-6 gene in an embryonic stem cell. The additional flanking AIP-6 nucleic acid is of sufficient length for successful homologous recombination with the endogenous gene. Typically, several kilobases of flanking DNA (both at the 5' and 3' ends) are included in the vector (see, e.g., Thomas and Capecchi (1987) Cell 51:503 for a description of homologous recombination vectors). The vector is introduced into an embryonic stem cell line (e.g., by electroporation) and cells in which the introduced AIP-6 gene has homologously recombined with the endogenous AIP-6 gene are selected (see, e.g., Li et al. (1992) Cell 69:915). The selected cells are then injected into a blastocyst of an animal (e.g., a mouse) to form aggregation chimeras (see, e.g., Bradley in Teratocarcinomas and Embryonic Stem Cells: A Practical Approach, Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) Current Opinion in Bio/Technology 2:823–829 and in PCT Publication Nos. WO 90/11354, WO 91/01140, WO 92/0968, and WO 93/04169.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) Proc. Natl. Acad. Sci. USA 89:6232–6236. Another example of a recombinase system is the FLP recombinase system of Saccharomyces cerevisiae (O'Gorman et al. (1991) Science 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) Nature 385:810–813 and PCT Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The AIP-6 nucleic acid molecules, AIP-6 proteins, and anti-AIP-6 antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a AIP-6 protein or anti-AIP-6 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see, e.g., Chen et al. (1994) Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) detection assays (e.g., chromosomal mapping, tissue typing, forensic biology), c) predictive medicine (e.g., diagnostic assays, prognostic assays, monitoring clinical trials, and pharmacogenomics); and d) methods of treatment (e.g., therapeutic and prophylactic). A AIP-6 protein interacts with other cellular proteins and can thus be used for (i) regulation of cellular proliferation; (ii) regulation of cellular differentiation; and (iii) regulation of cell survival. The isolated nucleic acid molecules of the invention can be used to express AIP-6 protein (e.g., via a recombinant expression vector in a host cell in gene therapy applications), to detect AIP-6 mRNA (e.g., in a biological sample) or a genetic lesion in a AIP-6 gene, and to modulate AIP-6 activity. In addition, the AIP-6 proteins can be used to screen drugs or compounds which modulate the AIP-6 activity or expression as well as to treat disorders characterized by insufficient or excessive production of AIP-6 protein or production of AIP-6 protein forms which have decreased or aberrant activity compared to AIP-6 wild type protein. In addition, the anti-AIP-6 antibodies of the invention can be used to detect and isolate AIP-6 proteins and modulate AIP-6 activity.

This invention further pertains to novel agents identified by the above-described screening assays and uses thereof for treatments as described herein.

A. Screening Assays

The invention provides a method (also referred to herein as a "screening assay") for identifying modulators, i.e., candidate or test compounds or agents (e.g., peptides, peptidomimetics, small molecules or other drugs) which bind to AIP-6 proteins or have a stimulatory or inhibitory effect on, for example, AIP-6 expression or AIP-6 activity.

In one embodiment, the invention provides assays for screening candidate or test compounds which bind to or modulate the activity of a AIP-6 protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Libraries of compounds may be presented in solution (e.g., Houghten (1992) Bio/Techniques 13:412–421), or on beads (Lam (1991) Nature 354:82–84), chips (Fodor (1993) Nature 364:555–556), bacteria (U.S. Pat. No. 5,223,409), spores (U.S. Pat. Nos. 5,571,698; 5,403,484; and 5,223, 409), plasmids (Cull et al. (1992) Proc. Natl. Acad. Sci. USA 89:1865–1869) or on phage (Scott and Smith (1990) Science 249:386–390; Devlin (1990) Science 249:404–406; Cwirla et al. (1990) Proc. Natl. Acad. Sci. 87:6378–6382; and Felici (1991) J. Mol. Biol. 222:301–310).

In one embodiment, an assay is a cell-based assay in which a cell which expresses a membrane-bound form of AIP-6 protein, or a biologically active portion thereof, on the cell surface is contacted with a test compound and the ability of the test compound to bind to a AIP-6 protein determined. The cell, for example, can be a yeast cell or a cell of mammalian origin. Determining the ability of the test compound to bind to the AIP-6 protein can be accomplished, for example, by coupling the test compound with a radioisotope or enzymatic label such that binding of the test compound to the AIP-6 protein or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In a preferred embodiment, the assay comprises contacting a cell which expresses a membrane-bound form of AIP-6 protein, or a biologically active portion thereof, on the cell surface with a known compound which binds AIP-6 to form an assay mixture, contacting the assay mixture with a test compound, and determining the ability of the test compound to interact with a AIP-6 protein, wherein determining the ability of the test compound to interact with a AIP-6 protein comprises determining the ability of the test compound to preferentially bind to AIP-6 or a biologically active portion thereof as compared to the known compound.

In another embodiment, an assay is a cell-based assay comprising contacting a cell expressing a membrane-bound form of AIP-6 protein, or a biologically active portion thereof, on the cell surface with a test compound and determining the ability of the test compound to modulate (e.g., stimulate or inhibit) the activity of the AIP-6 protein or biologically active portion thereof. Determining the ability of the test compound to modulate the activity of AIP-6 or a biologically active portion thereof can be accomplished, for example, by determining the ability of the AIP-6 protein to bind to or interact with a AIP-6 target molecule. As used herein, a "target molecule" is a molecule with which a AIP-6 protein binds or interacts in nature, for example, a molecule associated with the internal surface of a cell membrane or a cytoplasmic molecule. An AIP-6 target molecule can be a non-AIP-6 molecule or an AIP-6 protein or polypeptide of the present invention. In one embodiment, a AIP-6 target molecule is a component of the apoptotic signal transduction pathway which facilitates transduction of an apoptotic signal (e.g., a signal generated by binding to another apoptotic signalling molecule. The target, for example, can be a second intercellular protein which has catalytic activity or a protein which facilitates the association of downstream signaling molecules with AIP-6.

Determining the ability of the AIP-6 protein to bind to or interact with a AIP-6 target molecule can be accomplished by one of the methods described above for determining direct binding. In a preferred embodiment, determining the ability of the AIP-6 protein to bind to or interact with a AIP-6 target molecule can be accomplished by determining the activity of the target molecule. For example, the activity of the target molecule can be determined by detecting induction of a cellular second messenger of the target (e.g., intracellular $Ca^{2+}$, diacylglycerol, IP3, etc.), detecting catalytic/enzymatic activity of the target an appropriate substrate, detecting the induction of a reporter gene (e.g., a AIP-6-responsive regulatory element operatively linked to a nucleic acid encoding a detectable marker, e.g. luciferase), or detecting a cellular response, for example, cell survival, cellular differentiation, cell proliferation or cellular death.

In yet another embodiment, an assay of the present invention is a cell-free assay comprising contacting a AIP-6 protein or biologically active portion thereof with a test compound and determining the ability of the test compound to bind to the AIP-6 protein or biologically active portion thereof. Binding of the test compound to the AIP-6 protein can be determined either directly or indirectly as described above. In a preferred embodiment, the assay includes contacting the AIP-6 protein or biologically active portion thereof with a known compound which binds AIP-6 to form an assay mixture, contacting the assay mixture with a test compound, and determining the ability of the test compound to interact with a AIP-6 protein, wherein determining the ability of the test compound to interact with a AIP-6 protein comprises determining the ability of the test compound to preferentially bind to AIP-6 or biologically active portion thereof as compared to the known compound.

In another embodiment, an assay is a cell-free assay comprising contacting AIP-6 protein or biologically active portion thereof with a test compound and determining the ability of the test compound to modulate (e.g., stimulate or inhibit) the activity of the AIP-6 protein or biologically active portion thereof. Determining the ability of the test compound to modulate the activity of AIP-6 can be accomplished, for example, by determining the ability of the AIP-6 protein to bind to a AIP-6 target molecule by one of the methods described above for determining direct binding. In an alternative embodiment, determining the ability of the test compound to modulate the activity of AIP-6 can be accomplished by determining the ability of the AIP-6 protein to further modulate a AIP-6 target molecule. For example, the catalytic/enzymatic activity of the target molecule on an appropriate substrate can be determined as previously described.

In yet another embodiment, the cell-free assay comprises contacting the AIP-6 protein or biologically active portion thereof with a known compound which binds AIP-6 to form an assay mixture, contacting the assay mixture with a test compound, and determining the ability of the test compound to interact with a AIP-6 protein, wherein determining the ability of the test compound to interact with a AIP-6 protein comprises determining the ability of the AIP-6 protein to preferentially bind to or modulate the activity of a AIP-6 target molecule.

The cell-free assays of the present invention are amenable to use of both the soluble form or the membrane-bound form of AIP-6. In the case of cell-free assays comprising the membrane-bound form of AIP-6, it may be desirable to utilize a solubilizing agent such that the membrane-bound form of AIP-6 is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N, N-dimethyl-3-ammonio-1-propane sulfonate.

In more than one embodiment of the above assay methods of the present invention, it may be desirable to immobilize either AIP-6 or its target molecule to facilitate separation of complexed from uncomplexed forms of one or both of the proteins, as well as to accommodate automation of the assay. Binding of a test compound to AIP-6, or interaction of AIP-6 with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/AIP-6 fusion proteins or glutathione-S-transferase/target fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or AIP-6 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of AIP-6 binding or activity determined using standard techniques.

Other techniques for immobilizing proteins on matrices can also be used in the screening assays of the invention. For example, either AIP-6 or its target molecule can be immobilized utilizing conjugation of biotin and streptavidin. Biotinylated AIP-6 or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with AIP-6 or target molecules but which do not interfere with binding of the AIP-6 protein to its target molecule can be derivatized to the wells of the plate, and unbound target or AIP-6 trapped in the wells by antibody conjugation. Methods for detecting such complexes, in addition to those described above for the GST-immobilized complexes, include immunodetection of complexes using antibodies reactive with the AIP-6 or target molecule, as well as enzyme-linked assays which rely on detecting an enzymatic activity associated with the AIP-6 or target molecule.

In another embodiment, modulators of AIP-6 expression are identified in a method in which a cell is contacted with a candidate compound and the expression of AIP-6 mRNA or protein in the cell is determined. The level of expression of AIP-6 mRNA or protein in the presence of the candidate compound is compared to the level of expression of AIP-6 mRNA or protein in the absence of the candidate compound. The candidate compound can then be identified as a modulator of AIP-6 expression based on this comparison. For example, when expression of AIP-6 mRNA or protein is greater (statistically significantly greater) in the presence of the candidate compound than in its absence, the candidate compound is identified as a stimulator of AIP-6 mRNA or protein expression. Alternatively, when expression of AIP-6 mRNA or protein is less (statistically significantly less) in the presence of the candidate compound than in its absence, the candidate compound is identified as an inhibitor of AIP-6 mRNA or protein expression. The level of AIP-6 mRNA or protein expression in the cells can be determined by methods described herein for detecting AIP-6 mRNA or protein.

In yet another aspect of the invention, the AIP-6 proteins can be used as "bait proteins" in a two-hybrid assay or three hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Bio/Techniques* 14:920–924; Iwabuchi et al. (1993) *Oncogene* 8:1693–1696; and PCT Publication No. WO 94/10300), to identify other proteins, which bind to or interact with AIP-6 ("AIP-6-binding proteins" or "AIP-6-bp") and modulate AIP-6 activity. Such AIP-6-binding proteins are also likely to be involved in the propagation of signals by the AIP-6 proteins as, for example, upstream or downstream elements of the apoptotic signalling pathway.

The two-hybrid system is based on the modular nature of most transcription factors, which consist of separable DNA-binding and activation domains. Briefly, the assay utilizes two different DNA constructs. In one construct, the gene that codes for AIP-6 is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an AIP-6-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with AIP-6.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. Accordingly, AIP-6 nucleic acid molecules described herein or fragments thereof, can be used to map the location of AIP-6 genes on a chromosome. The mapping of the AIP-6 sequences to chromosomes is an important first step in correlating these sequences with genes associated with disease.

Briefly, AIP-6 genes can be mapped to chromosomes by preparing PCR primers (preferably 15–25 bp in length) from the AIP-6 sequences. Computer analysis of AIP-6 sequences can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the AIP-6 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the AIP-6 sequences to design oligonucleotide primers, sublocalization can be achieved with panels of fragments from specific chromosomes. Other mapping strategies which can similarly be used to map a AIP-6 sequence to its chromosome include in situ hybridization (described in Fan et al. (1990) *Proc. Natl. Acad. Sci. USA* 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., (Human Chromosomes: A Manual of Basic Techniques (Pergamon Press, New York, 1988)).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) *Nature*, 325:783–787.

Moreover, differences in the DNA sequences between individuals affected and unaffected with a disease associated with the AIP-6 gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The AIP-6 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the AIP-6 sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The AIP-6 sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can comfortably provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from AIP-6 sequences described herein is used to generate a unique identification database for an individual, those same reagents can later be used to identify tissue from that individual. Using the unique identification database, positive identification of the individual, living or dead, can be made from extremely small tissue samples.

3. Use of Partial AIP-6 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 are particularly appropriate for this use as greater numbers of polymorphisms occur in the noncoding regions, making it easier to differentiate individuals using this technique. Examples of polynucleotide reagents include the AIP-6 sequences or portions thereof, e.g., fragments derived from the noncoding regions of SEQ ID NO:1 having a length of at least 20 or 30 bases.

The AIP-6 sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such AIP-6 probes can be used to identify tissue by species and/or by organ type.

In a similar fashion, these reagents, e.g., AIP-6 primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trails are used for prognostic (predictive) purposes to thereby treat an individual prophylactically. Accordingly, one aspect of the present invention relates to diagnostic assays for determining AIP-6 protein and/or nucleic acid expression as well as AIP-6 activity, in the context of a biological sample (e.g., blood, serum, cells, tissue) to thereby determine whether an individual is afflicted with a disease or disorder, or is at risk of developing a disorder, associated with aberrant AIP-6 expression or activity. The invention also provides for prognostic (or predictive) assays for determining whether an individual is at risk of developing a disorder associated with AIP-6 protein, nucleic acid expression or activity. For example, mutations in a AIP-6 gene can be assayed in a biological sample. Such assays can be used for prognostic or predictive purpose to thereby prophylactically treat an individual prior to the onset of a disorder characterized by or associated with AIP-6 protein, nucleic acid expression or activity.

Another aspect of the invention provides methods for determining AIP-6 protein, nucleic acid expression or AIP-6 activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs or other compounds) on the expression or activity of AIP-6 in clinical trials.

These and other agents are described in further detail in the following sections.

1. Diagnostic Assays

An exemplary method for detecting the presence or absence of AIP-6 in a biological sample involves obtaining a biological sample from a test subject and contacting the biological sample with a compound or an agent capable of detecting AIP-6 protein or nucleic acid (e.g., mRNA, genomic DNA) that encodes AIP-6 protein such that the presence of AIP-6 is detected in the biological sample. A preferred agent for detecting AIP-6 mRNA or genomic DNA is a labeled nucleic acid probe capable of hybridizing to AIP-6 mRNA or genomic DNA. The nucleic acid probe can be, for example, a full-length AIP-6 nucleic acid, such as the nucleic acid of SEQ ID NO: 1 or 3, or a portion thereof, such as an oligonucleotide of at least 15, 30, 50, 100, 250 or 500 nucleotides in length and sufficient to specifically hybridize under stringent conditions to AIP-6 mRNA or genomic DNA. Other suitable probes for use in the diagnostic assays of the invention are described herein.

A preferred agent for detecting AIP-6 protein is an antibody capable of binding to AIP-6 protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect AIP-6 mRNA, protein, or genomic DNA in a biological sample in vitro as well as in vivo. For example, in vitro techniques for detection of AIP-6 mRNA include Northern hybridizations and in situ hybridizations. In vitro techniques for detection of AIP-6 protein include enzyme linked immunosorbent assays (ELISAs), Western blots, immunoprecipitations and immunofluorescence. In vitro techniques for detection of AIP-6 genomic DNA include Southern hybridizations. Furthermore, in vivo techniques for detection of AIP-6 protein include introducing into a subject a labeled anti-AIP-6 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject.

In another embodiment, the methods further involve obtaining a control biological sample from a control subject, contacting the control sample with a compound or agent capable of detecting AIP-6 protein, mRNA, or genomic DNA, such that the presence of AIP-6 protein, mRNA or genomic DNA is detected in the biological sample, and comparing the presence of AIP-6 protein, mRNA or genomic DNA in the control sample with the presence of AIP-6 protein, mRNA or genomic DNA in the test sample.

The invention also encompasses kits for detecting the presence of AIP-6 in a biological sample (a test sample). Such kits can be used to determine if a subject is suffering from or is at increased risk of developing a disorder associated with aberrant expression of AIP-6 (e.g., an immunological disorder). For example, the kit can comprise a labeled compound or agent capable of detecting AIP-6 protein or mRNA in a biological sample and means for determining the amount of AIP-6 in the sample (e.g., an anti-AIP-6 antibody or an oligonucleotide probe which binds to DNA encoding AIP-6, e.g., SEQ ID NO:1 or SEQ ID NO:3). Kits may also include instruction for observing that the tested subject is suffering from or is at risk of developing a disorder associated with aberrant expression of AIP-6 if the amount of AIP-6 protein or mRNA is above or below a normal level.

For antibody-based kits, the kit may comprise, for example: (1) a first antibody (e.g., attached to a solid support) which binds to AIP-6 protein; and, optionally, (2) a second, different antibody which binds to AIP-6 protein or the first antibody and is conjugated to a detectable agent.

For oligonucleotide-based kits, the kit may comprise, for example: (1) a oligonucleotide, e.g., a detectably labelled oligonucleotide, which hybridizes to a AIP-6 nucleic acid sequence or (2) a pair of primers useful for amplifying a AIP-6 nucleic acid molecule;

The kit may also comprise, e.g., a buffering agent, a preservative, or a protein stabilizing agent. The kit may also comprise components necessary for detecting the detectable agent (e.g., an enzyme or a substrate). The kit may also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of AIP-6.

2. Prognostic Assays

The methods described herein can furthermore be utilized as diagnostic or prognostic assays to identify subjects having or at risk of developing a disease or disorder associated with aberrant AIP-6 expression or activity. For example, the assays described herein, such as the preceding diagnostic assays or the following assays, can be utilized to identify a subject having or at risk of developing a disorder associated with AIP-6 protein, nucleic acid expression or activity. Alternatively, the prognostic assays can be utilized to identify a subject having or at risk for developing such a disease or disorder. Thus, the present invention provides a method in which a test sample is obtained from a subject and AIP-6 protein or nucleic acid (e.g., mRNA, genomic DNA) is detected, wherein the presence of AIP-6 protein or nucleic acid is diagnostic for a subject having or at risk of developing a disease or disorder associated with aberrant AIP-6 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant AIP-6 expression or activity. For example, such methods can be used to determine whether a subject can be effectively treated with a specific agent or class of agents (e.g., agents of a type which decrease AIP-6 activity). Thus, the present invention provides methods for determining whether a subject can be effectively treated with an agent for a disorder associated with aberrant AIP-6 expression or activity in which a test sample is obtained and AIP-6 protein or nucleic acid is detected (e.g., wherein the presence of AIP-6 protein or nucleic acid is diagnostic for a subject that can be administered the agent to treat a disorder associated with aberrant AIP-6 expression or activity).

The methods of the invention can also be used to detect genetic lesions or mutations in a AIP-6 gene, thereby determining if a subject with the lesioned gene is at risk for a disorder characterized by aberrant cell proliferation and/or differentiation. In preferred embodiments, the methods include detecting, in a sample of cells from the subject, the presence or absence of a genetic lesion characterized by at least one of an alteration affecting the integrity of a gene encoding a AIP-6-protein, or the mis-expression of the AIP-6 gene. For example, such genetic lesions can be detected by ascertaining the existence of at least one of 1) a deletion of one or more nucleotides from a AIP-6 gene; 2) an addition of one or more nucleotides to a AIP-6 gene; 3) a substitution of one or more nucleotides of a AIP-6 gene, 4) a chromosomal rearrangement of a AIP-6 gene; 5) an alteration in the level of a messenger RNA transcript of a AIP-6 gene, 6) aberrant modification of a AIP-6 gene, such as of the methylation pattern of the genomic DNA, 7) the presence of a non-wild type splicing pattern of a messenger RNA transcript of a AIP-6 gene, 8) a non-wild type level of a AIP-6-protein, 9) allelic loss of a AIP-6 gene, and 10) inappropriate post-translational modification of a AIP-6-protein. As described herein, there are a large number of assay techniques known in the art which can be used for detecting lesions in a AIP-6 gene.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the AIP-6-gene (see, e.g., Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a AIP-6 gene under conditions such that hybridization and amplification of the AIP-6-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) *Proc. Natl. Acad. Sci. USA* 87:1874–1878), transcriptional amplification system (Kwoh, et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a AIP-6 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in AIP-6 can be identified by hybridizing a sample and control nucleic acids, e.g., DNA or RNA, to high density arrays containing hundreds or thousands of oligonucleotides probes (Cronin et al. (1996) *Human Mutation* 7:244–255; Kozal et al. (1996) *Nature Medicine* 2:753–759). For example, genetic mutations in AIP-6 can be identified in two-dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the AIP-6 gene and detect mutations by comparing the sequence of the sample AIP-6 with the corresponding wild-type (control) sequence. Examples of sequencing reactions include those based on techniques developed by Maxim and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the AIP-6 gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type AIP-6 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al (1988) *Proc. Natl Acad Sci USA* 85:4397; Saleeba et al (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in AIP-6 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a AIP-6 sequence, e.g., a wild-type AIP-6 sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in AIP-6 genes. For example, single strand conformation polymorphism (SSCP) may be used to detect differences in electrophoretic mobility between mutant and wild type nucleic acids (Orita et al. (1989) *Proc Natl. Acad. Sci USA*: 86:2766, see also Cotton (1993) *Mutat. Res.* 285:125–144; and Hayashi (1992) *Genet Anal Tech Appl* 9:73–79). Single-stranded DNA fragments of sample and control AIP-6 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition, it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a AIP-6 gene.

Furthermore, any cell type or tissue in which AIP-6 is expressed may be utilized in the prognostic assays described herein.

3. Pharmacogenomics

Agents, or modulators which have a stimulatory or inhibitory effect on AIP-6 activity (e.g., AIP-6 gene expression) as identified by a screening assay described herein can be administered to individuals to treat (prophylactically or therapeutically) disorders (e.g., an immunological disorder) associated with aberrant AIP-6 activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of AIP-6 protein, expression of AIP-6 nucleic acid, or mutation content of AIP-6 genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of AIP-6 protein, expression of AIP-6 nucleic acid, or mutation content of AIP-6 genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a AIP-6 modulator, such as a modulator identified by one of the exemplary screening assays described herein.

4. Monitoring of Effects During Clinical Trials

Monitoring the influence of agents (e.g., drugs, compounds) on the expression or activity of AIP-6 (e.g., the ability to modulate aberrant cell proliferation and/or differentiation) can be applied not only in basic drug screening, but also in clinical trials. For example, the effectiveness of an agent determined by a screening assay as described herein to increase AIP-6 gene expression, protein levels, or upregulate AIP-6 activity, can be monitored in clinical trails of subjects exhibiting decreased AIP-6 gene expression, protein levels, or downregulated AIP-6 activity. Alternatively, the effectiveness of an agent determined by a screening assay to decrease AIP-6 gene expression, protein levels, or downregulated AIP-6 activity, can be monitored in clinical trails of subjects exhibiting increased AIP-6 gene expression, protein levels, or upregulated AIP-6 activity. In such clinical trials, the expression or activity of AIP-6 and, preferably, other genes that have been implicated in, for example, a cellular proliferation disorder can be used as a "read out" or markers of the immune responsiveness of a particular cell.

For example, and not by way of limitation, genes, including AIP-6, that are modulated in cells by treatment with an agent (e.g., compound, drug or small molecule) which modulates AIP-6 activity (e.g., identified in a screening assay as described herein) can be identified. Thus, to study the effect of agents on cellular proliferation disorders, for example, in a clinical trial, cells can be isolated and RNA prepared and analyzed for the levels of expression of AIP-6 and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of AIP-6 or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a AIP-6 protein, mRNA, or genomic DNA in the preadministration sample; (iii) obtaining one or more post-administration samples from the subject; (iv) detecting the level of expression or activity of the AIP-6 protein, mRNA, or genomic DNA in the post-administration samples; (v) comparing the level of expression or activity of the AIP-6 protein, mRNA, or genomic DNA in the pre-administration sample with the AIP-6 protein, mRNA, or genomic DNA in the post administration sample or samples; and (vi) altering the administration of the agent to the subject accordingly. For example, increased administration of the agent may be desirable to increase the expression or activity of AIP-6 to higher levels than detected, i.e., to increase the effectiveness of the agent. Alternatively, decreased administration of the agent may be desirable to decrease expression or activity of AIP-6 to lower levels than detected, i.e., to decrease the effectiveness of the agent.

C. Methods of Treatment

The present invention provides for both prophylactic and therapeutic methods of treating a subject at risk of (or susceptible to) a disorder or having a disorder associated with aberrant AIP-6 expression or activity. Such disorders include cancer, autoimmune disorders, viral infections and neurological disorders.

1. Prophylactic Methods

In one aspect, the invention provides a method for preventing in a subject, a disease or condition associated with an aberrant AIP-6 expression or activity, by administering to the subject an agent which modulates AIP-6 expression or at least one AIP-6 activity. Subjects at risk for a disease which is caused or contributed to by aberrant AIP-6 expression or activity can be identified by, for example, any or a combination of diagnostic or prognostic assays as described herein. Administration of a prophylactic agent can occur prior to the manifestation of symptoms characteristic of the AIP-6 aberrancy, such that a disease or disorder is prevented or, alternatively, delayed in its progression. Depending on the type of AIP-6 aberrancy, for example, a AIP-6 agonist or AIP-6 antagonist agent can be used for treating the subject. The appropriate agent can be determined based on screening assays described herein.

2. Therapeutic Methods

Another aspect of the invention pertains to methods of modulating AIP-6 expression or activity for therapeutic purposes. The modulatory method of the invention involves contacting a cell with an agent that modulates one or more of the activities of AIP-6 protein activity associated with the cell. An agent that modulates AIP-6 protein activity can be an agent as described herein, such as a nucleic acid or a protein, a naturally-occurring cognate ligand of a AIP-6 protein, a peptide, a AIP-6 peptidomimetic, or other small molecule. In one embodiment, the agent stimulates one or more of the biological activities of AIP-6 protein. Examples of such stimulatory agents include active AIP-6 protein and a nucleic acid molecule encoding AIP-6 that has been introduced into the cell. In another embodiment, the agent inhibits one or more of the biological activities of AIP-6 protein. Examples of such inhibitory agents include anti-sense AIP-6 nucleic acid molecules and anti-AIP-6 antibodies. These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of a AIP-6 protein or nucleic acid molecule. In one embodiment, the method involves administering an agent (e.g., an agent identified by a screening assay described herein), or combination of agents that modulates (e.g., upregulates or downregulates) AIP-6 expression or activity. In another embodiment, the method involves administering a AIP-6 protein or nucleic acid molecule as therapy to compensate for reduced or aberrant AIP-6 expression or activity.

Stimulation of AIP-6 activity is desirable in situations in which AIP-6 is abnormally downregulated and/or in which increased AIP-6 activity is likely to have a beneficial effect. Conversely, inhibition of AIP-6 activity is desirable in situations in which AIP-6 is abnormally upregulated and/or in which decreased AIP-6 activity is likely to have a beneficial effect.

This invention is further illustrated by the following examples which should not be construed as limiting. The contents of all references, patents and published patent applications cited throughout this application are hereby incorporated by reference.

EXAMPLES

Example 1

Isolation and Characterization of Human AIP-6 cDNAs

The human amino acid sequences for X-IAP and cIAP-1 were used to search the proprietary and dbEST databases using TBLASTN (Wash U. version, 2.0, BLOSUM62 search matrix), and all sequences scoring better than 60 were saved. Sequences identified in this manner were assembled using Phrap (P. Green, U. Washington) and the sequences from the assembly compared back to the public and proprietary protein databases using BLASTX (Wash U. version 2.0, BLOSUM62 search matrix). Sequences exhibiting 90% or better identity to any protein present in Genpept, SwissProt, or PIR were marked as examples of these proteins and removed. The remaining sequences were compared back to the proprietary EST and dBEST databases using BLASTN (Wash U. version 2.0, mismatch score of −10, minimum score of 300) to identify overlapping EST's. This search led to the identification of 2 overlapping ESTs (51755 and 166716), both of which contained a Ring finger domain.

The following protocol was used to clone AIP-6. The host strain Y1090Zl containing the human fetal brain ZIPLOX bacteriophage cDNA library was plated on NZY plates at a density of 50,000 cfu. After overnight incubation of 37° C. the plaques were transferred in duplicate to Hybond-N membranes (Amersham) using standard procedures. PCR was used to amplify a portion of the AIP-6/mining entry 4846 EST, and after gel-purification the PCR product was extracted using the QiaQuick Gel Extraction Kit (Qiagen, Valencia, Calif.) and labelled with $^{32}$P-dCTP using the Prime-IT RmT kit (Stratagene; La Jolla, Calif.). After pre-hybridization in Church Buffer for 1 hr at 65° C., the membranes were hybridized in Church buffer containing the labelled probe overnight at the same temperature. The membranes were then washed three times in 2×SSC/0.1% SDS at 65° C. Subsequent washes at 65° C. were performed in 1×SSC/0.1% SDS for 30 min and 0.2×SSC/0.1% SDS. Positive plaques appearing on duplicate membranes were picked and resuspended in SM (containing chloroform). The identified plaques were further purified by a secondary screen using the procedure described above. Positive plaques identified by secondary screening were verified by full-length sequencing.

The sequence of the full length AIP-6 cDNA (FIGS. 1A–1B; SEQ ID NO:1) was found to have an open reading frame (ORF) (SEQ ID NO:3), extending from nucleotide 104 to nucleotide 1219 encoding a 372 amino acid gene product, AIP-6 (FIG. 2; SEQ ID NO:2).

Example 2

Distribution of AIP-6 mRNA in Human Tissues

The expression of AIP-6 was analyzed using Northern blot hybridization. A portion of AIP-6 cDNA encoding the amino terminus of AIP-6 protein was generated by PCR using a forward primer (f) and reverse primer (r), e.g., AGTCCGAAGCTTACCATGAAGGCGGTGC-CACGTCTATGTGGGCT (f) (SEQ ID NO:21) and CCG-TACTAGTCTAGACTAGGACTTGAA-CACGTGCACGGCTCGCAC (r) (SEQ ID NO:22). The PCR product was gel-purified and labelled using the Bright-Star Psoralenbiotin Labelling Kit (Ambion). mRNA Human Tissue Blot II (#7759-1) or the Human Cancer Cell Line Blot (#7757-1) (Clontech) were pre-hybridized in Complete Nylon Wash Solution for 1 hr at 67° C. Hybridization with the labelled probe was performed in Complete Nylon Wash Solution overnight at 67° C. The blots were washed three times in 0.5×Complete Nylon Wash Solution, with each wash for 30 min at 67° C. Detection of the biotin labelled DNA probe was performed using the BrightStar Biodetect Kit (Ambion), and exposure against Biomax MR (Kodak) film.

These studies revealed that AIP-6 is expressed as an approximate 2.2 kilobase transcript. AIP-6 is constitutively expressed at a low level in many human tissues (including the spleen, thymus, prostate, ovary, and small intestine colon), and moderately expressed in the testis, and not expressed in peripheral blood leukocytes.

Expression of AIP-6 was shown to be low in cancer cell line Burkitt lymphoma Raji, and moderately expressed in melanoma G361 and highly expressed in promyelocyte leukemia HL-60, hela Cell S3, chronic myelogenous leukemia K-562, lymphoblastic leukemia Molt-4, colorectal adenocarcinoma SW480 and lung carcinoma SW480.

Example 3

Characterization of AIP-6 Proteins

In this example, the predicted amino acid sequence of human AIP-6 protein was compared to amino acid sequences of known AIP proteins and a RING finger domain was identified (FIG. 3). In addition, the molecular weight of the human AIP-6 proteins was predicted to be 42 KDa.

The human AIP-6 cDNA isolated as described above (FIGS. 1A–1B; SEQ ID NO:1) encodes a 372 amino acid protein (FIG. 2; SEQ ID NO:2).

As shown in FIG. 3, AIP-6 has a region (amino acids 359–393; SEQ ID NO:2) of homology to a RING finger domain of D-iap (accession number L49441; SEQ ID NO:5), D-IAP (accession number u45881; SEQ ID NO:6), D-IHA (accession number u38809; SEQ ID NO:7), D-ilp (accession number u32373; SEQ ID NO:8), H-ciap1 (accession number q13489; SEQ ID NO:9), H-ciap2 (accession number q13490; SEQ ID NO:10), H-Xiap (accession number u45880; SEQ ID NO:11), M-miha (accession number u36842; SEQ ID NO:12), C. elegans cosmid (accession number u40945; SEQ ID NO:13), D-Neuralized (accession number u12593; SEQ ID NO:14), (H-Cell growth reg/accession number u66469; SEQ ID NO:15), C. elegans/chrom III (accession number z77655; SEQ ID NO:16), C. elegans F16A11.1 (accession number z81505; SEQ ID NO:17), V-C. iridescent/IAP (accession number AF003534; SEQ ID NO:18).

AIP-6 has a predicted MW of 42 kDa, not including post-translational modifications.

Example 4

Preparation of AIP-6 Proteins

Recombinant AIP-6 can be produced in a variety of expression systems. For example, the mature AIP-6 peptide can be expressed as a recombinant glutathione-S-transferase (GST) fusion protein in *E. coli* and the fusion protein can be isolated and characterized. Specifically, as described above, AIP-6 can be fused to GST and this fusion protein can be expressed in *E. coli* strain PEB199. Expression of the GST-AIP-6 fusion protein in PEB199 can be induced with IPTG. The recombinant fusion protein can be purified from crude bacterial lysates of the induced PEB199 strain by affinity chromatography on glutathione beads.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid molecule comprising a nucleotide sequence which encodes a polypeptide comprising at least 150 contiguous amino acid residues of SEQ ID NO:2, wherein the polypeptide is an apoptosis inhibitor.

2. The nucleic acid molecule of claim 1 wherein the nucleic acid molecule comprises a nucleotide sequence which encodes a polypeptide comprising at least 300 contiguous amino acid residues of SEQ ID NO:2.

3. An isolated nucleic acid molecule which hybridizes to the complement of a nucleic acid molecule consisting of SEQ ID NO:3 under conditions of incubation at 45° C. in 6.0×SSC followed by washing in 0.2×SSC, 0.1% SDS at 50° C., the isolated nucleic acid molecule comprising at least 500 nucleotides, wherein the nucleic acid molecule encodes a polypeptide that is a apoptosis inhibitor.

4. An isolated nucleic acid molecule which hybridizes to the complement of the nucleic acid molecule consisting of SEQ ID NO:3 under conditions of incubation at 45° C. in 6.0×SSC followed by washing in 0.2×SSC, 0.1% SDS at 65° C., the isolated nucleic acid molecule comprising at least 500 nucleotides, wherein the nucleic acid molecule encodes a polypeptide that is a apoptosis inhibitor.

5. An isolated nucleic acid molecule comprising 500 contiguous nucleotides of SEQ ID NO:3, wherein the nucleic acid molecule encodes a polypeptide that is a apoptosis inhibitor.

6. The isolated nucleic acid molecule of claim 5 comprising the nucleotide sequence of SEQ ID NO:3.

7. The isolated nucleic acid molecule of claim 6 consisting of the nucleotide sequence of SEQ ID NO:3.

8. An isolated nucleic acid molecule comprising a nucleotide sequence encoding a polypeptide comprising the amino acid sequence of SEQ ID NO:2, wherein the nucleic acid molecule encodes a polypeptide that is a apoptosis inhibitor.

9. The isolated nucleic acid molecule of claim 8 comprising a nucleotide sequence encoding a polypeptide consisting of the amino acid sequence of SEQ ID NO:2.

10. An isolated nucleic acid molecule comprising a nucleotide sequence which is at least 85% identical to the nucleotide sequence of SEQ ID NO:3, wherein the percent identity is determined using the NBLAST program with a score of 100 and a word length of 12, wherein the nucleic acid molecule encodes a polypeptide that is a apoptosis inhibitor.

11. The nucleic acid molecule of claim 10, wherein the nucleotide sequence is at least 95% identical to the nucleotide sequence of SEQ ID NO:3, wherein the percent identity is determined using the NBLAST program with a score of 100 and a word length of 12.

12. A vector comprising the nucleic acid molecule of any of claims 1–4 and 5–11.

13. The vector of claim 12, which includes nucleic acid sequences which regulate expression of a polypeptide encoded by the nucleic acid molecule.

14. A host cell comprising the vector of claim 12.

15. A host cell comprising the vector of claim 13.

16. A host cell comprising the nucleic acid molecule of any of claims 1–4 and 5–11.

17. The host cell of claim 14 which is a mammalian host cell.

18. The host cell of claim 15 which is a mammalian host cell.

19. The host cell of claim 16 which is a mammalian host cell.

20. A method for producing a polypeptide comprising culturing the host cell of claim 15 under conditions in which the nucleic acid molecule is expressed.

* * * * *